United States Patent
Uehara

(10) Patent No.: US 10,981,034 B1
(45) Date of Patent: *Apr. 20, 2021

(54) COMPANION DEVICE TO SUPPORT QUALIFYING MOVEMENT IDENTIFICATION

(71) Applicant: Alert Core, Inc., Kailua, HI (US)

(72) Inventor: Gregory Takeo Uehara, Kailua, HI (US)

(73) Assignee: Alert Core, Inc., Kailua, HI (US)

( * ) Notice: Subject to any disclaimer, the term of this patent is extended or adjusted under 35 U.S.C. 154(b) by 288 days.

This patent is subject to a terminal disclaimer.

(21) Appl. No.: 14/800,931

(22) Filed: Jul. 16, 2015

Related U.S. Application Data

(63) Continuation-in-part of application No. 14/789,136, filed on Jul. 1, 2015, now Pat. No. 9,706,962, and a continuation-in-part of application No. 14/132,808, filed on Dec. 18, 2013, now Pat. No. 9,226,706.

(60) Provisional application No. 61/739,160, filed on Dec. 19, 2012, provisional application No. 62/019,522, filed on Jul. 1, 2014, provisional application No. 62/025,804, filed on Jul. 17, 2014.

(51) Int. Cl.
*A63B 24/00* (2006.01)
*A61B 5/11* (2006.01)
*A61B 5/00* (2006.01)

(52) U.S. Cl.
CPC ............ *A63B 24/0062* (2013.01); *A61B 5/11* (2013.01); *A61B 5/1123* (2013.01); *A61B 5/6823* (2013.01); *A61B 5/6824* (2013.01); *A63B 2024/0071* (2013.01)

(58) Field of Classification Search
None
See application file for complete search history.

(56) References Cited

U.S. PATENT DOCUMENTS

| | | | | |
|---|---|---|---|---|
| 5,755,674 A | * | 5/1998 | Watson | A61B 5/0404 600/587 |
| 6,413,190 B1 | * | 7/2002 | Wood | A61B 5/1071 463/36 |
| 9,226,706 B2 | * | 1/2016 | Uehara | G06F 19/3481 |
| 9,795,337 B2 | * | 10/2017 | Uehara | A61B 5/1121 |
| 2007/0015976 A1 | * | 1/2007 | Miesel | A61B 5/0006 600/301 |

(Continued)

*Primary Examiner* — Matthew Kremer
(74) *Attorney, Agent, or Firm* — Staniford Tomita LLP

(57) ABSTRACT

A system includes companion device that has movement sensors and a separate wearable device that has core contraction sensors. The companion device can be coupled to moving objects such as exercise equipment. Signals from the companion device and wearable device sensors are transmitted to a processor which analyzes the object movement signals and determines when a qualifying movement is performed which benefits from core contraction. Signals from the core contraction sensors are also transmitted to the processor and are used to determine if the core is contracted during the qualifying movement. If the core is contracted during the qualifying movement, the movement is a protected qualifying movement. However, if the core is not contracted during the qualifying movement the movement is an unprotected qualifying movement. The system can inform the user when unprotected qualifying movements are performed.

12 Claims, 23 Drawing Sheets

(56) References Cited

U.S. PATENT DOCUMENTS

| | | | |
|---|---|---|---|
| 2009/0062696 A1* | 3/2009 | Nathan | A61B 5/1107 600/595 |
| 2009/0298605 A1* | 12/2009 | Wiegers | A63B 69/3608 473/199 |
| 2010/0280336 A1* | 11/2010 | Giftakis | A61B 5/0476 600/301 |
| 2011/0054782 A1* | 3/2011 | Kaahui | A63B 69/3608 701/532 |
| 2011/0269601 A1* | 11/2011 | Nelson | A47C 7/021 482/8 |
| 2012/0245439 A1* | 9/2012 | Andre | A61B 5/0205 600/310 |

* cited by examiner

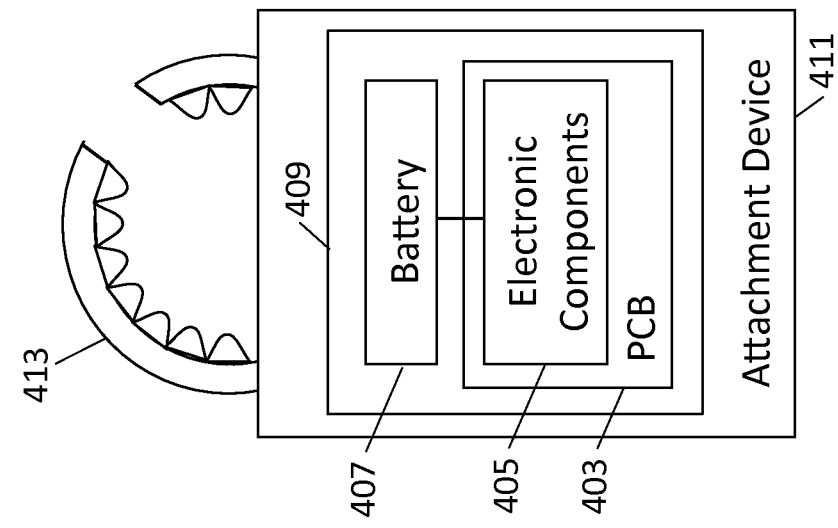
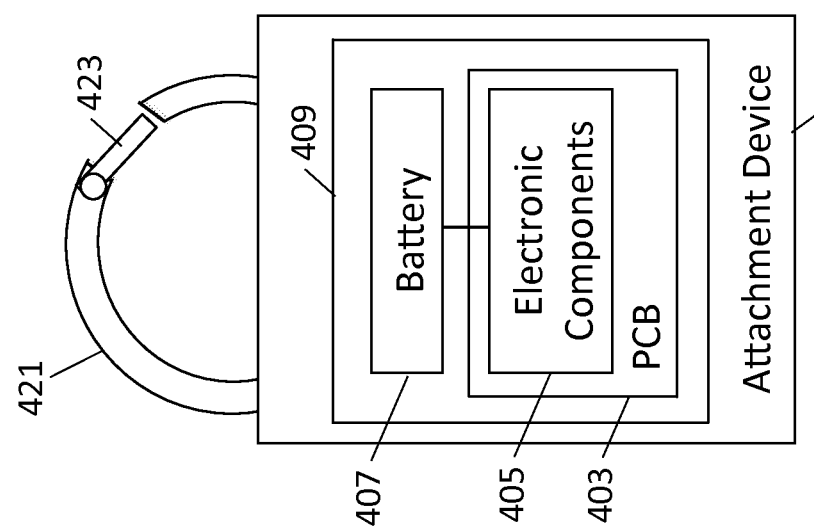
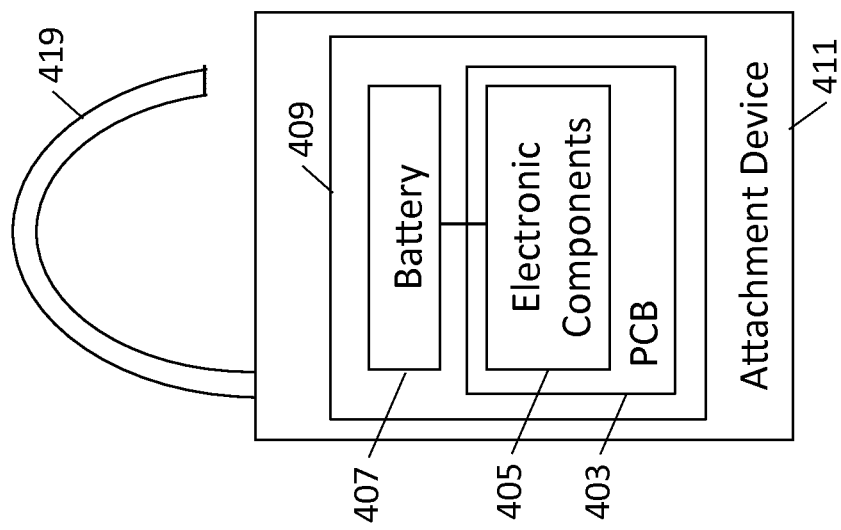

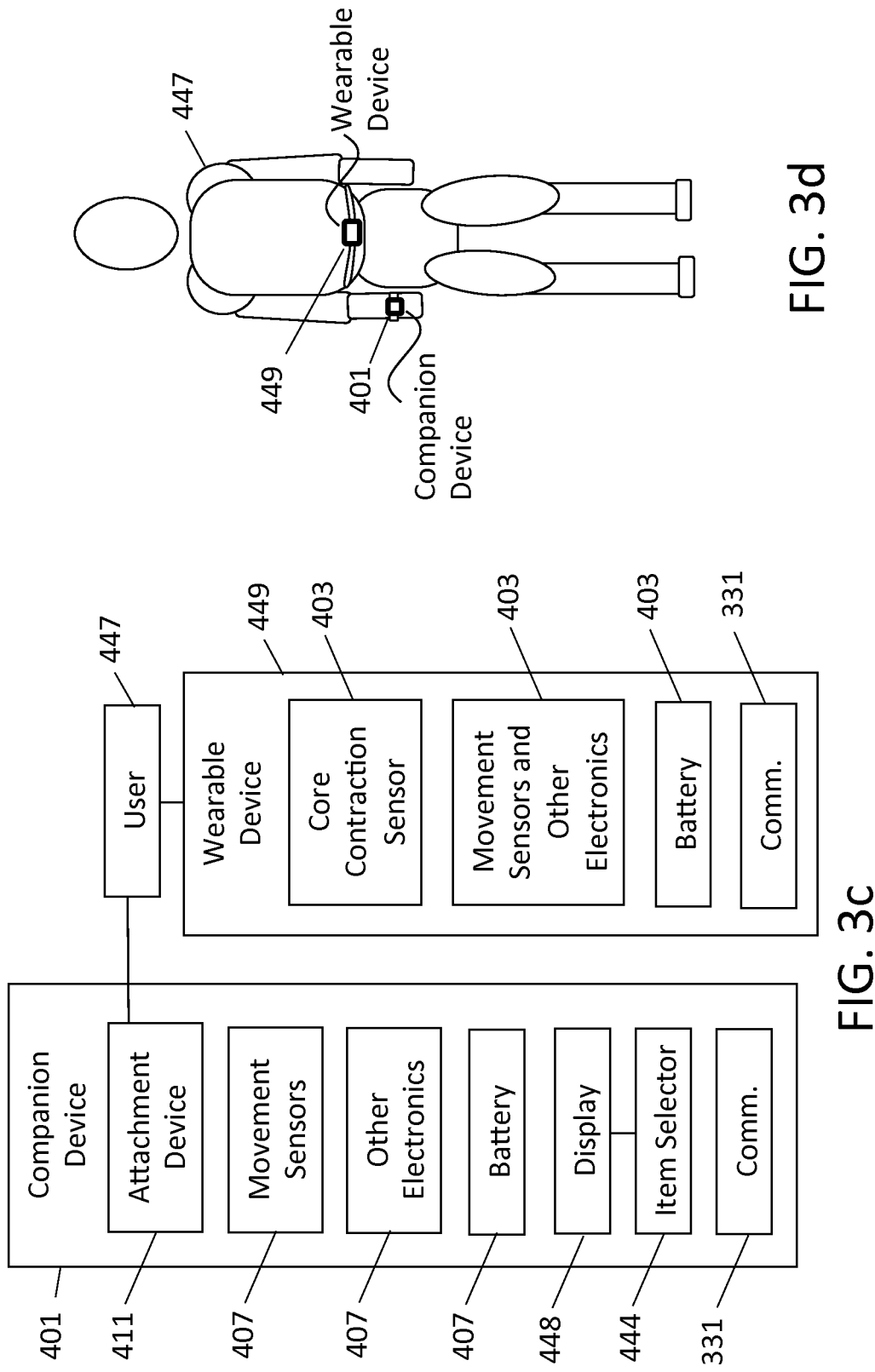

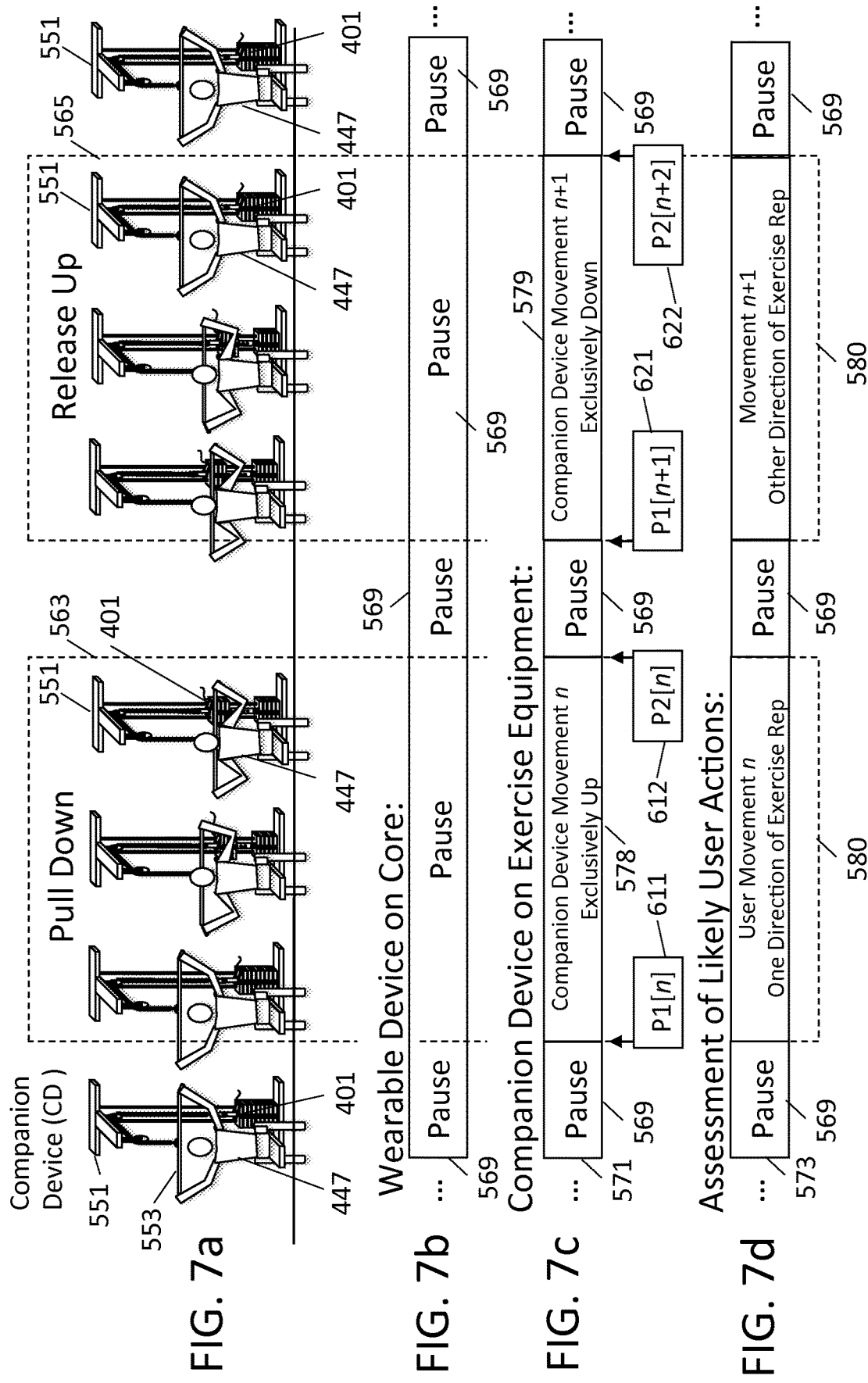

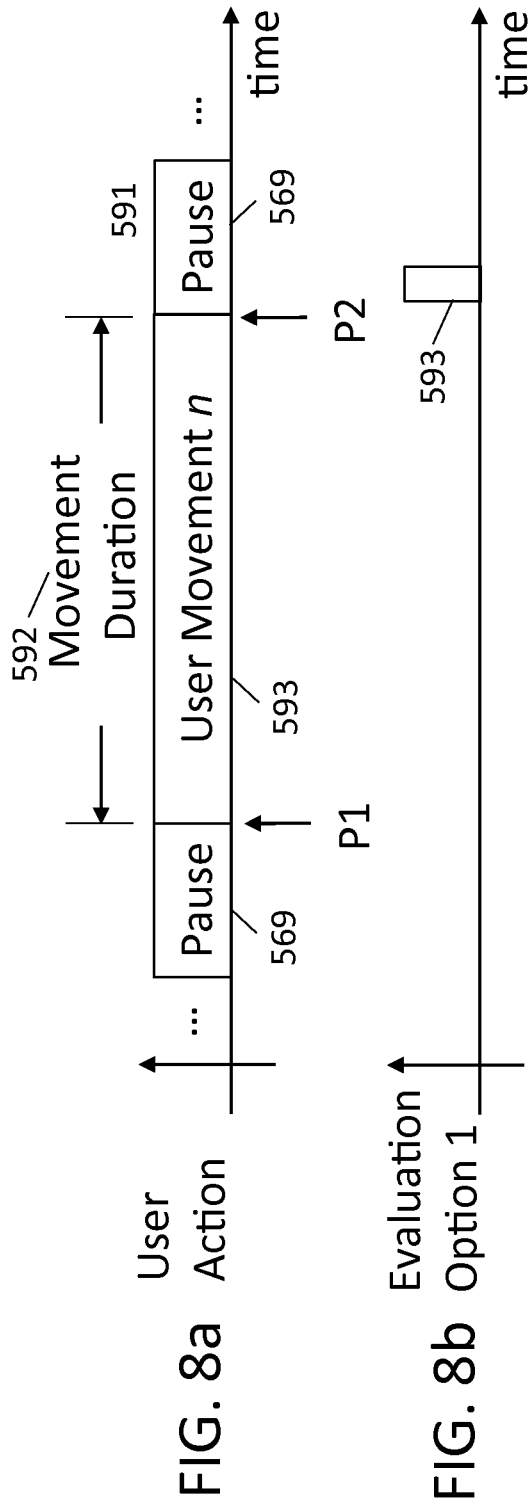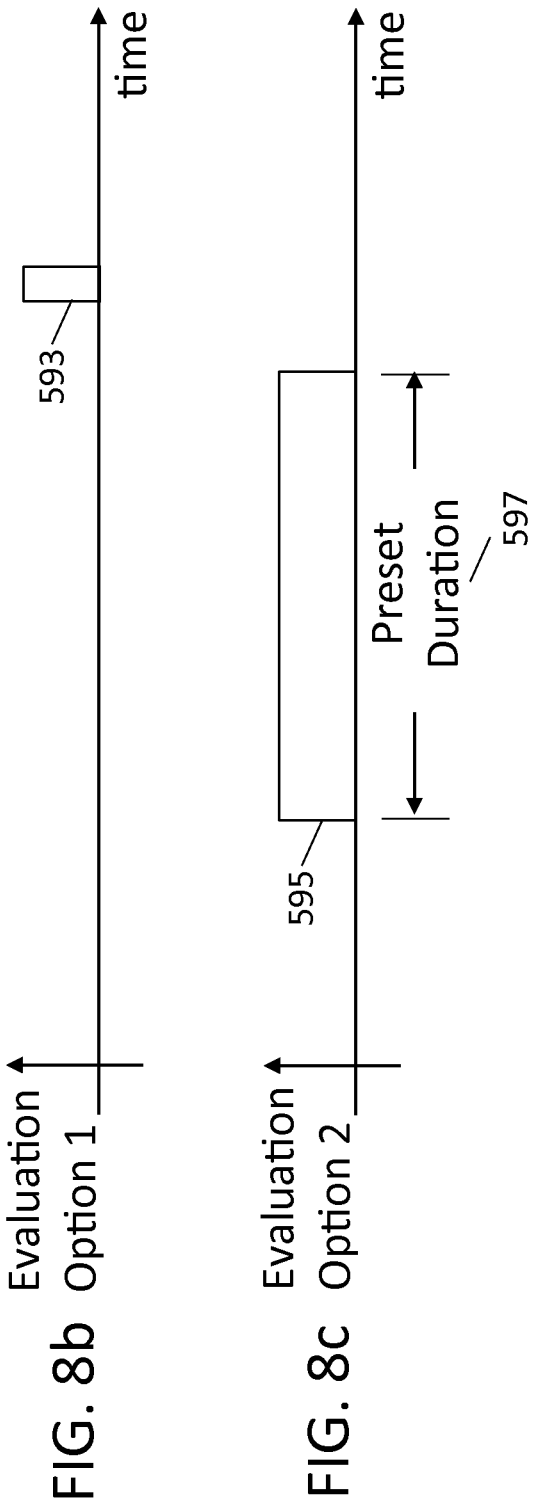

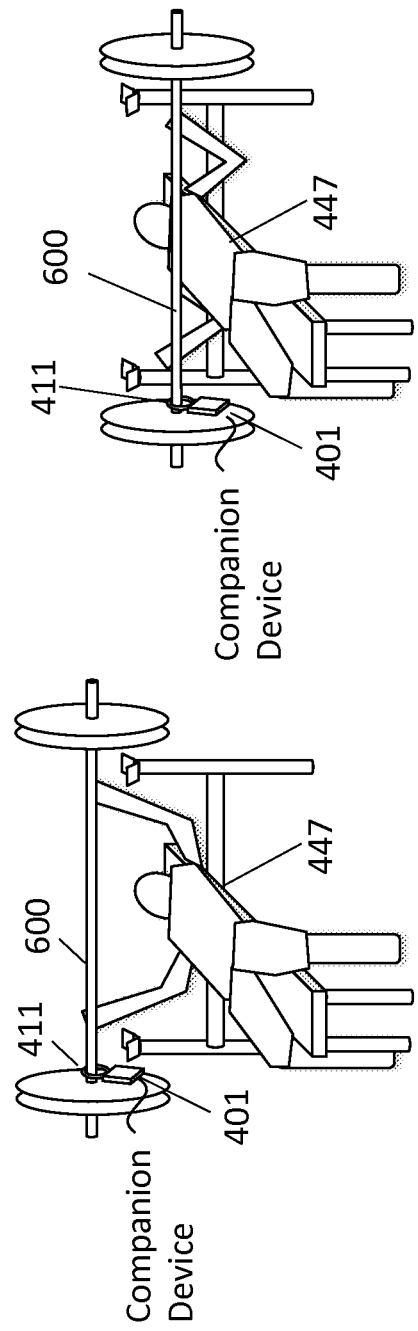

COMPANION DEVICE TO SUPPORT QUALIFYING MOVEMENT IDENTIFICATION

CROSS-REFERENCE TO RELATED APPLICATIONS

This application claims priority to U.S. Patent Application No. 62/025,804, "Companion Device To Support Qualifying Movement Identification" filed Jul. 17, 2014. This application is also a continuation in part of U.S. patent application Ser. No. 14/789,136 entitled "Apparatus And Method For Teaching And Algorithms For Identifying Qualifying Movements" filed Jul. 1, 2015 which claims priority to U.S. Patent Application No. 62/019,522 entitled "Apparatus And Method For Teaching And Algorithms For Identifying Qualifying Movements" filed Jul. 1, 2014. This application is also a continuation in part of U.S. patent application Ser. No. 14/132,808, "System, Apparatus, And Method For Promoting Usage Of Core Muscles And Other Applications", filed Dec. 18, 2013, which claims priority to U.S. Provisional Application No. 61/739,160, "System For Promoting Usage Of Core Muscles And Other Applications", filed Dec. 19, 2012. U.S. patent application Ser. Nos. 14/789,136, 14/132,808, 61/739,160, 62/019,522 and 62/025,804 are hereby incorporated by reference in their entirety.

FIELD OF THE INVENTION

Embodiments disclosed relate to systems, methods and devices for development of support from core muscles by identifying user movements, and by detecting core muscle usage in conjunction with those identified movements. Embodiments also relate to discriminating between multiple identified movements, recognizing core muscle activity or lack of it thereof in those identified movements, and providing feedback to the user regarding a correct or incorrect core muscle use, acknowledging a core muscle use when appropriate, informing of an inappropriate core muscle use, and identifying a movement wherein a core muscle is not used but could be used. Embodiments relate to a companion device that may operate with a wearable device to encourage core usage when exercising, training with exercise equipment, and practicing and performing athletic movements.

BACKGROUND

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also be embodiments of the invention.

In recent years, there has been explosive growth in the number of portable and handheld devices that include but are not limited to sensors such as accelerometers, gyros, magnetometers, altimeters, and/or pressure sensors. Examples of such devices include smart phones, cell phones, gaming devices, and wearable devices (or wearables).

In gaming devices, tilt or angles of rotation are often tracked and used to control elements of the game. A large number of wearables target health and fitness applications where steps taken and flights of stairs taken are tracked utilizing accelerometers and altimeters.

Inertial navigation is a method utilizing accelerometers, gyroscopes or gyros, and a microprocessor contained on a moving object to continuously calculate via dead reckoning the position, orientation, and velocity of the object. Dead reckoning is the process of calculating the current position by using a previously determined position and advancing that position based on estimated speeds over elapsed time. A system implementing inertial navigation is self-contained and requires no external references. Up until recently, inertial navigation has generally been used mainly by ocean craft, aircraft, guided missiles, and spacecraft. Inertial navigation may be used in embodiments of the inventive concepts described in this disclosure targeting systems and devices for the wearables market.

Most health and fitness wearables on the market today may track one or more of the following: steps taken, number of stairs taken, heart rate, movement activity, and sleep patterns. These devices generally utilize accelerometers, altimeters, light sources and sensors, and voltage sensors to sense and detect the parameters they measure and track. Generally, these wearables do not require the combination of position and orientation tracking that may require algorithms utilized in inertial navigation.

SUMMARY

Let us define a Qualifying Movement or QM as a movement for which support from the contraction of the core muscles may be beneficial to support and protect the lumbosacral junction and the lumbar spine. Furthermore, let us define QM Identification or QM ID as the method, process, principles, approach and/or concepts utilized to evaluate the available data to make a determination whether or not a user utilizing the inventive system has executed a Qualifying Movement.

U.S. patent application Ser. No. 14/132,808 includes descriptions of systems that can comprise a wearable device which monitors a user's movements for Qualifying Movements and the user's core muscles for contraction of the core. When a Qualifying Movement is identified, based on the status of the user's core before, during, and after the Qualifying Movement, the system may determine whether or not the Qualifying Movement is protected or not protected. If the user's core is contracted adequately starting before and through the movement, the Qualifying Movement may be determined to be protected. If the core is not contracted over an adequate time period(s) around the Qualifying Movement, the movement may be determined to be not protected. Based upon the result of the determination of the movement being protected or not protected, the system may signal to the user in order aid the user in developing procedural memory to utilize their core to protect their lumbar spine and lumbosacral junction during such Qualifying Movements.

Additional inventive features are described in U.S. patent application Ser. No. 14/132,808 including: wearable devices, wrist devices and smart watches. In different embodiments, the system can use wearable device with exercise equipment utilizing pulleys. The sensor(s) can be placed on the pulley(s) that rotate when a user performs an exercise on equipment containing pulleys. The sensor(s) can detect rotation of the pulleys and this movement may be identified as a Qualifying Movement. The sensor or sensors detecting pulley rotation during exercise movements may encourage users to build the desired procedural memory for support of the lumbosacral junction through core contraction during execution of the exercises. In an embodiment, the system can be used with a wrist device or smart watch that may be used, in part, to identify arm movements while performing gym exercises on machines exercise devices not containing pulleys, for example free weights with dumbbells or barbells and identifying certain movements as Qualifying Movements.

U.S. patent application Ser. Nos. 14/789,136 and 62/019,522 include descriptions of teaching approaches for users to develop said procedural memory for core support while performing every day movements. In addition, a comprehensive approach for algorithm development for identifying Qualifying Movements in every day movements which operate on the outputs of sensors contained in a wearable device is described.

In this present disclosure, a companion device is described that functions with the system as well as algorithms for processing signals from the companion device. The companion device may be attached to different attachment mechanisms which can be coupled to moving components of exercise machines or attachment devices such as a wrist strap. The signal processing of the signals from the companion device can be extensions of the comprehensive approach for algorithm design for Qualifying Movement Identification described in U.S. patent application Ser. Nos. 14/789,136 and 62/019,522 to systems employing the wearable device described in U.S. patent application Ser. No. 14/132,808 and the companion device described in this disclosure.

The role of the core muscles for stabilizing the region of the lumbosacral junction during certain movements can be widely encouraged by a number of disciplines including physical therapy, occupational therapy, personal training, strength training, fitness training, crossfit, yoga, pilates, and tai-chi. The stabilizing role of the core muscles has also been identified to be critical in athletics to add strength and power.

In some physical therapy practices and/or sessions, therapists may have their clients perform exercises as part of the rehabilitation process. Sometimes, these exercises are performed on the same or similar exercise machines often found in exercise and gym facilities. When rehabilitating back pain, one of the procedures physical therapists may have their clients perform is to contract their core during the exertion portions of exercises. Most exercises have at least two movements, preferably with a pause in between, where one movement is a push, pull, or lift from a first position to a second position, and the other movement is a return to the first position. Depending upon the exercise and the condition of the user including the fitness level and condition of pain (if any), the user may be encouraged to utilize their core through one or both movements, or continuously throughout the entire repetition or exercise.

There are at least two advantages to utilizing the core during exercise movements. First, the lumbosacral junction and lumbar spine are supported during the exercises. This may limit the possibility of any or further injury while strengthening the muscles being exercised. And second, the client may practice utilizing their core during movements where their muscles are lightly, moderately, to heavily loaded and develop procedural memory to utilize their core in all movements, and particularly Qualifying Movements. Many physical therapists encourage their clients to contract their core prior to and during movements including movements such as sit-to-stand (sitting down from a standing position) and stand-to-sit (standing up from a sitting position). Many of the teaching practices used by physical therapists as just described may also be used by other disciplines including occupational therapist, physiatrists, and personal, fitness, and strength trainers.

Emphasizing and monitoring core contractions during exercise requires a highly interactive session between a therapist or trainer (refer to as therapist) and a patient or client (refer to as client) in order to continually remind and monitor the client to contract their core muscles before and during movements. Due to practical difficulties such as placing a hand on the client's core while the client is moving, such monitoring is seldom done due to the inconveniences. So while the objective of monitoring the core muscles during gym exercises and providing feedback to the client, particularly when they fail to utilize their core muscles during exercise movements is desirable, it is not pursued in a significant way, in part, due to the lack of availability of effective and convenient tools, devices, or systems.

The pulley based system described in U.S. patent application Ser. No. 14/132,808 may be implemented with one device containing sensors and a means for communication placed on or near one pulley and the wearable device. These devices coupling to the pulleys may be installed on each exercise machine or select exercise machines in a gym. When multiple users are simultaneously using multiple pieces of exercise equipment, implementation of the communication protocol between any one user's wearable device and the specific piece of exercise equipment that user may be on may cumbersome to implement. In some applications, it may be attractive instead to have a device that performs the function of the pulley based system, but that can be moved from exercise machine to exercise machine as the user moves and that also includes a means for communicating with the wearable device. Such a system may be convenient to use in a gym environment with multiple users and multiple exercise machines and equipment. Furthermore, with training provided by appropriate software running on a smart device or training mechanisms such as workshops or online videos, the system may be utilized by individuals during their personal therapy and exercise sessions.

This invention disclosure describes a system to encourage and develop a user's support from their core muscles during exercises utilizing commonly used exercise equipment available in most gyms, exercise facilities, and therapy facilities equipped with exercise equipment. The inventive system may be utilized by trainers and therapists such as personal trainers and physical therapists with their clients and patients to increase proper and habitual usage of the core when performing strengthening and fitness exercises.

In this disclosure, a companion device to the wearable device is described. In one embodiment, this companion device may take on different specific forms for different applications where a form may include an electronics element including a PCB with sensors, at least one microprocessor, electronics capable of communicating over at least one communication protocol like Bluetooth or Zigbee, and a battery; as well as a second element including a mechanism to attach the companion device to exercise equipment, part of the user's body, or another item as may be desirable to meet the objectives of an application of the inventive system.

In another embodiment, the companion device may be configured to attach to a movable element on exercise equipment such as the weight stack, bar, rope, or chain on an exercise machine or to a barbell, dumbbell, or kettlebell. The attachment may be through an open ring with a slot, a hook, a ring with a movable section that can move to enable the ring to slide onto or off of an object, or another structure enabling a temporary attachment onto a cylindrical shape, aforementioned movable elements, or similar.

In another embodiment, the companion device may be configured to attach to a body part of the user such as one of the user's arms, legs, or head. The attachment may be via a wrist strap, leg strap, head band, helmet, or similar appropriate method depending on the application. A smart watch is an example of an embodiment of the companion device having movement sensors and a transmitter that is configured to attach to a user's wrist.

In another embodiment, the companion device may be configured to attach to any element of an exercise device in which the movement of the element resulting from a physical action of a user may coincide with a desired contraction of the user's core muscles, thus creating an equivalence between the movement of the element and a Qualifying Movement.

In another embodiment, the companion device may be configured to identify a Qualifying Movement based on change in orientation or movement of the device or change in orientation and movement of the device.

In another embodiment, the companion device may be configured to identify a Qualifying Movement based on the orientation and/or movement of the companion device together with the orientation and/or movement of a wearable device where the timing relationships of the orientations and/or movements of the two devices are utilized in the identification of a Qualifying Movement.

In another embodiment, the companion device may be configured to identify a Qualifying Movement based on the orientation and/or movement of the companion device together with the orientation and/or movement of one or more of a similar device and/or the orientation and/or movement of a wearable device where the timing relationships of the orientations and/or movements of the different devices are utilized in the identification of a Qualifying Movement.

Embodiments of the inventive devices and systems presented in this disclosure may address each of the short comings of currently available products and system solutions. In some applications, more than one companion device may be utilized in the system.

Embodiments disclosed include a system and method for development and use of core muscles' support during exercising, comprising a means for identifying a user qualifying movement when utilizing exercise equipment, a means for detecting a core muscle contraction in the identified qualifying movement, a means for discriminating between a core muscle contraction and no core muscle contraction in the identified qualifying movement; and a means to provide feedback to the user.

FIG. if illustrates a block diagram of an embodiment of a companion device with a gapped ring.

Figure 1C:
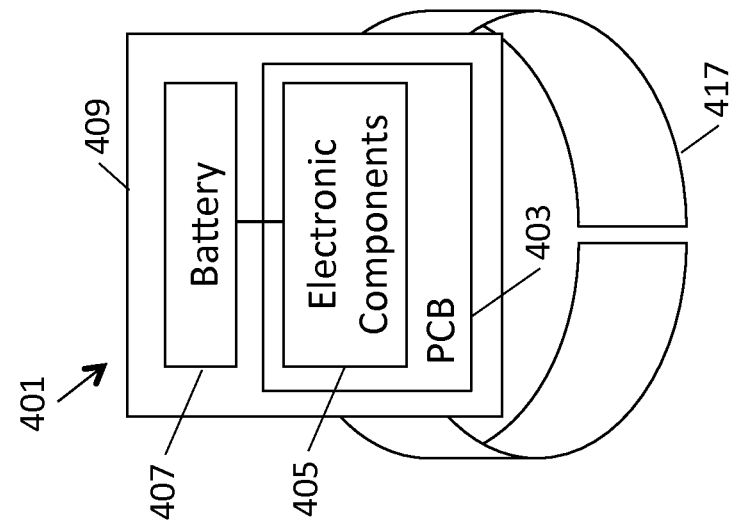
FIG. 1c illustrates a block diagram of an embodiment of a companion device with a wrist band.
Figure 1B:
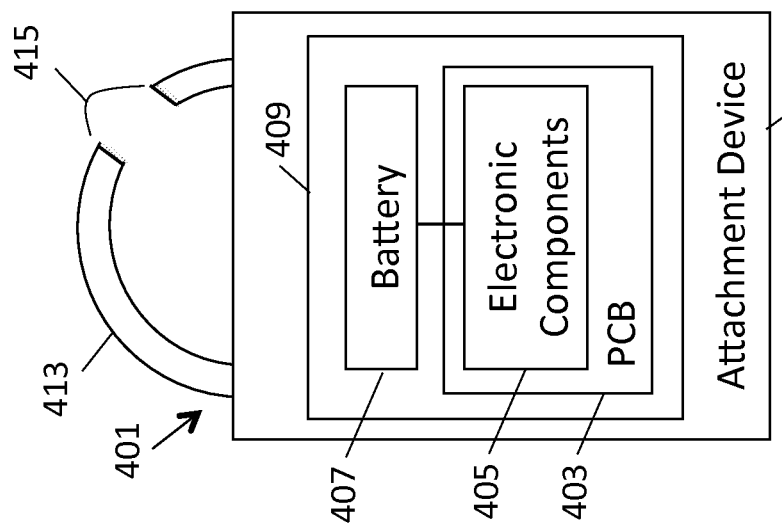
FIG. 1b illustrates a block diagram of an embodiment of a companion device with an attachment device.
Figure 1A:
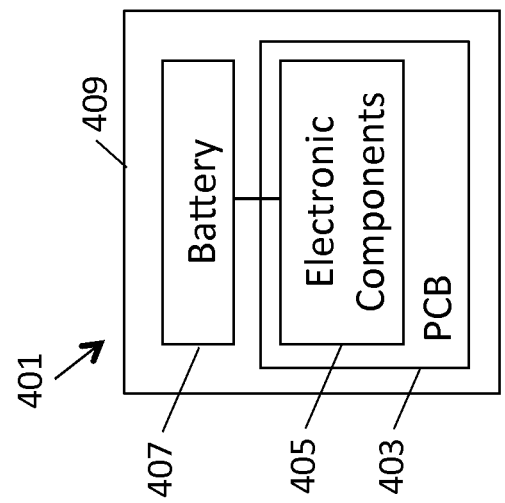
FIG. 1a illustrates a block diagram of an embodiment of a companion device.
Figure 1I:
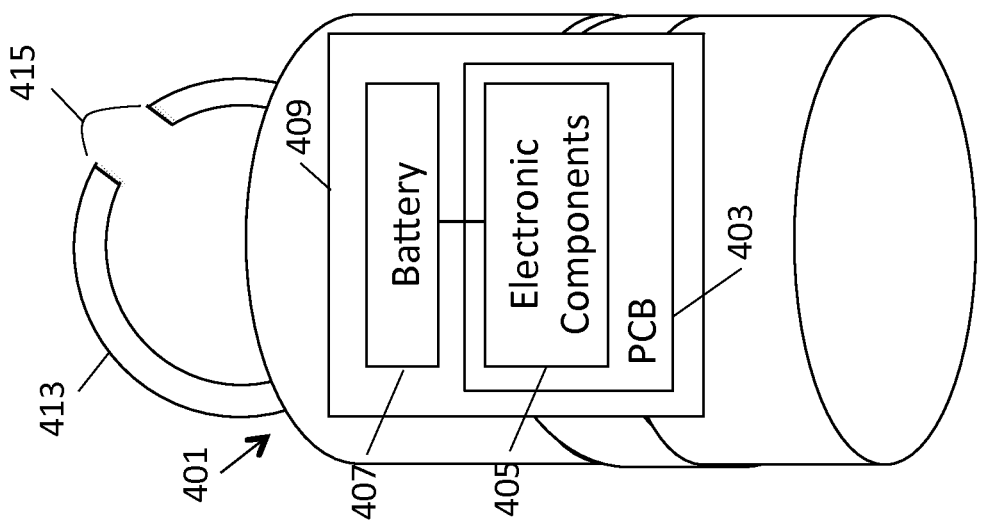
FIG. 1d illustrates a block diagram of an embodiment of a companion device with a hook.
FIG. 1e illustrates a block diagram of an embodiment of a companion device with a ring.
Figure 1H:
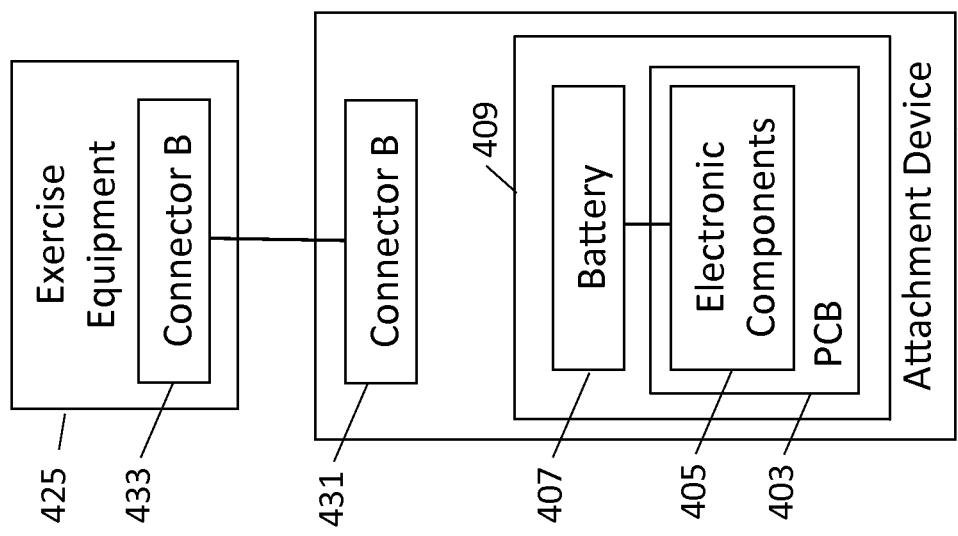
Figure 1G:
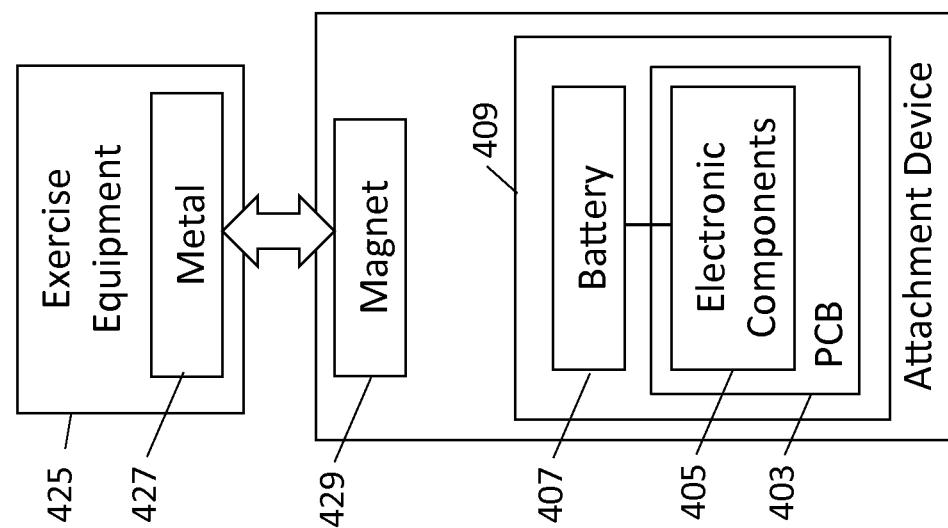

FIG. 1g illustrates a block diagram of an embodiment of a companion device with a magnet.

FIG. 1h illustrates a block diagram of an embodiment of a companion device with a connector.

FIG. 1i illustrates a block diagram of a smart watch embodiment of a companion device with a gapped ring.

Figure 2:
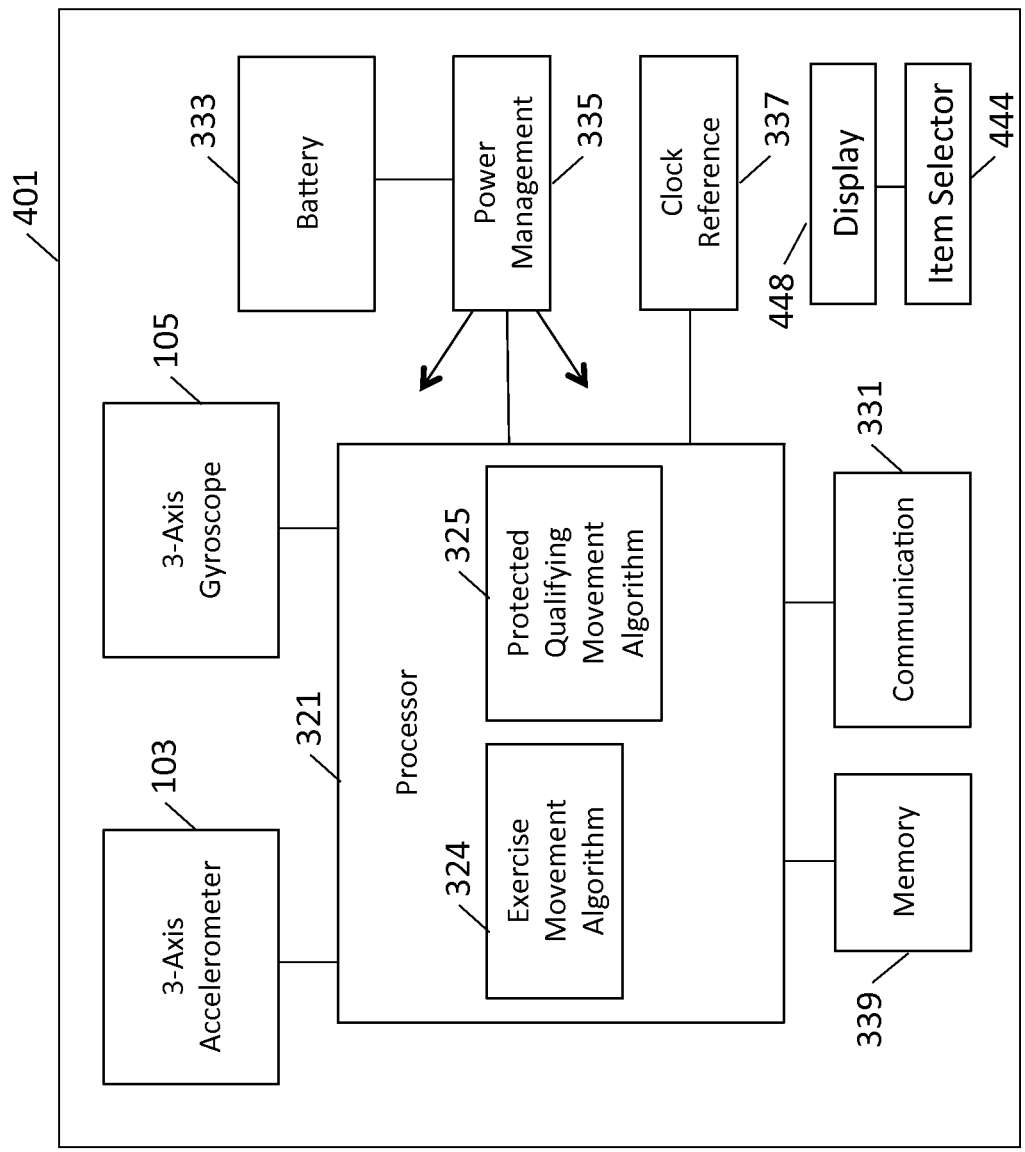

FIG. 2 illustrates a block diagram of an embodiment of a companion device.

Figure 3A:
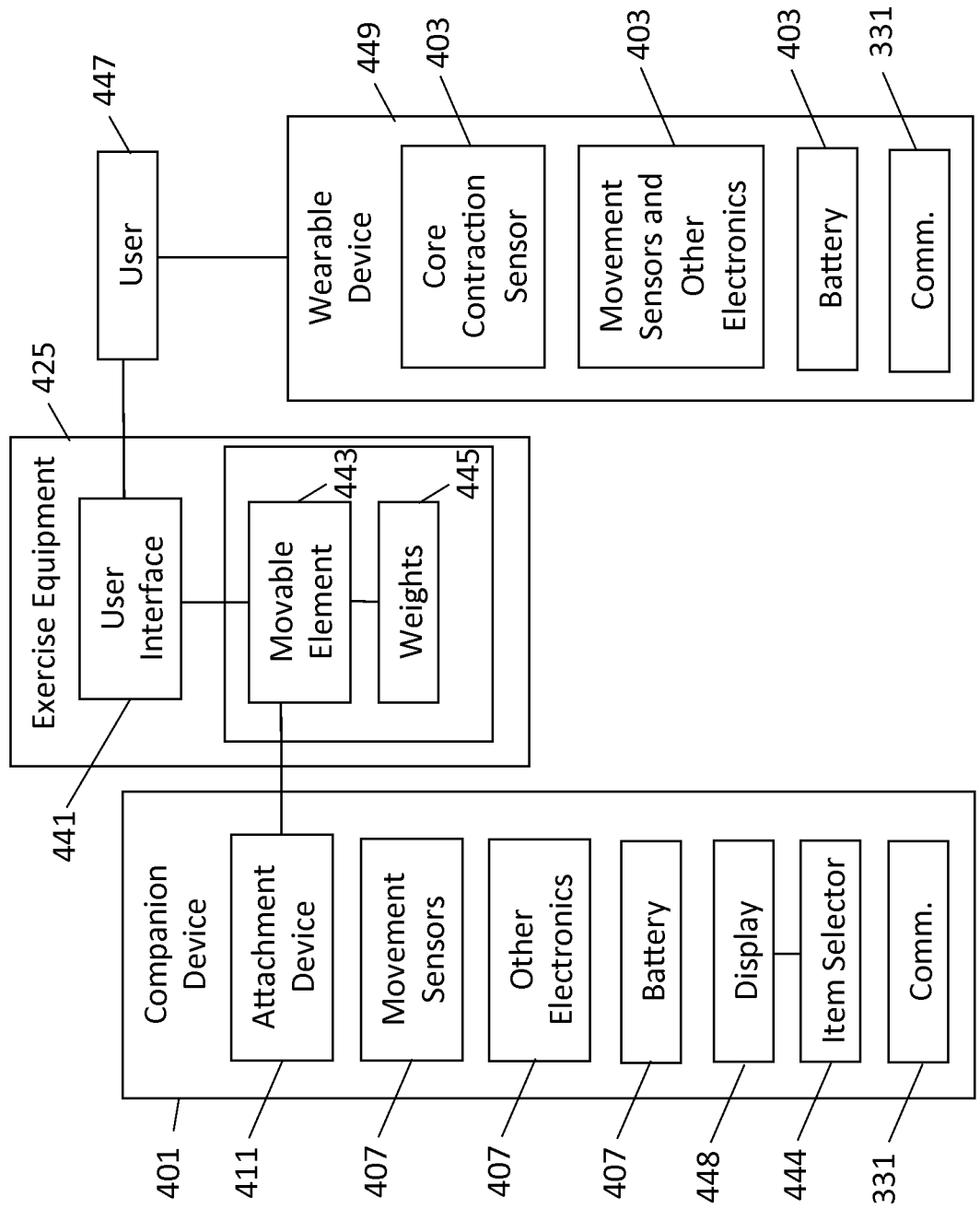
Figure 3B:
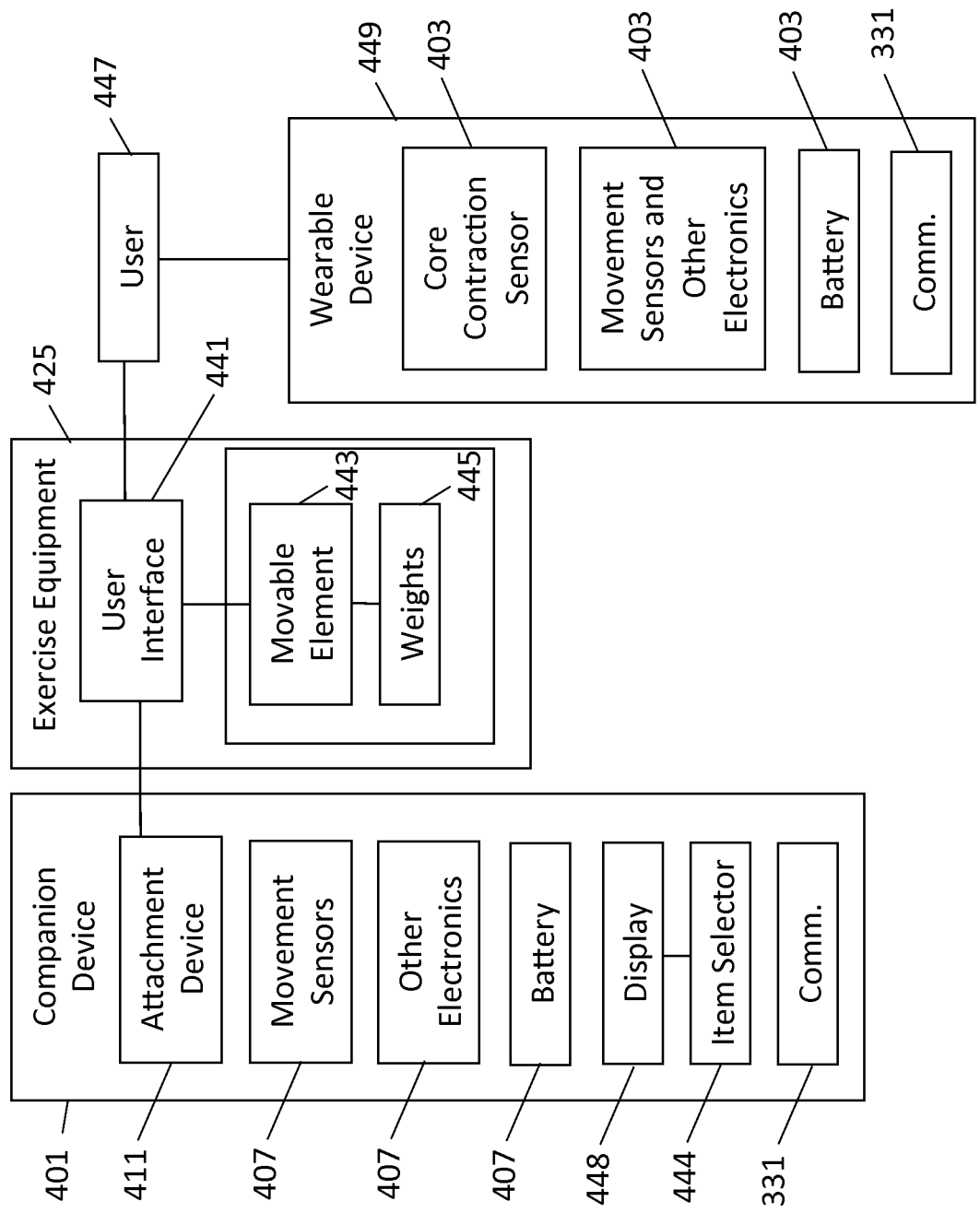

FIGS. 3a and 3b illustrate bock diagrams of embodiments of systems that include a companion device, exercise equipment and a wearable device.

FIG. 3c illustrate a block diagram of an embodiment of a system that includes a companion device and a wearable device.

FIG. 3d illustrates a front view of a user with a companion device and a wearable device.

Figure 4B:
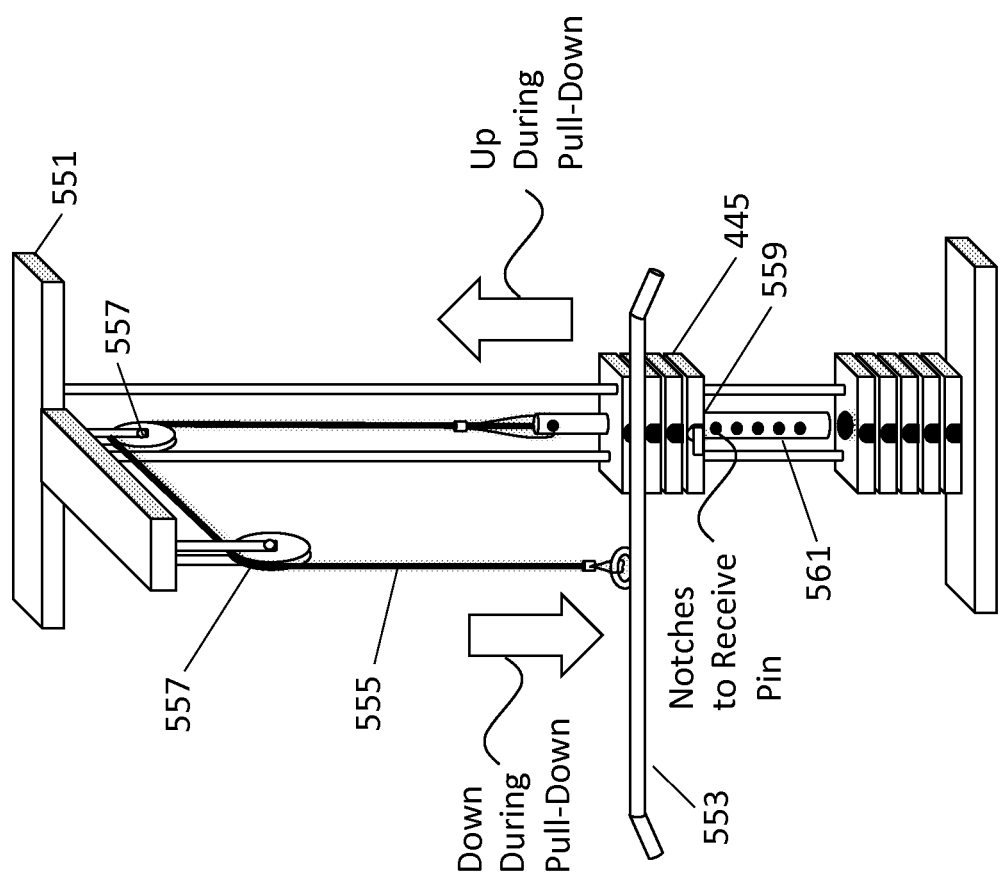
Figure 4A:
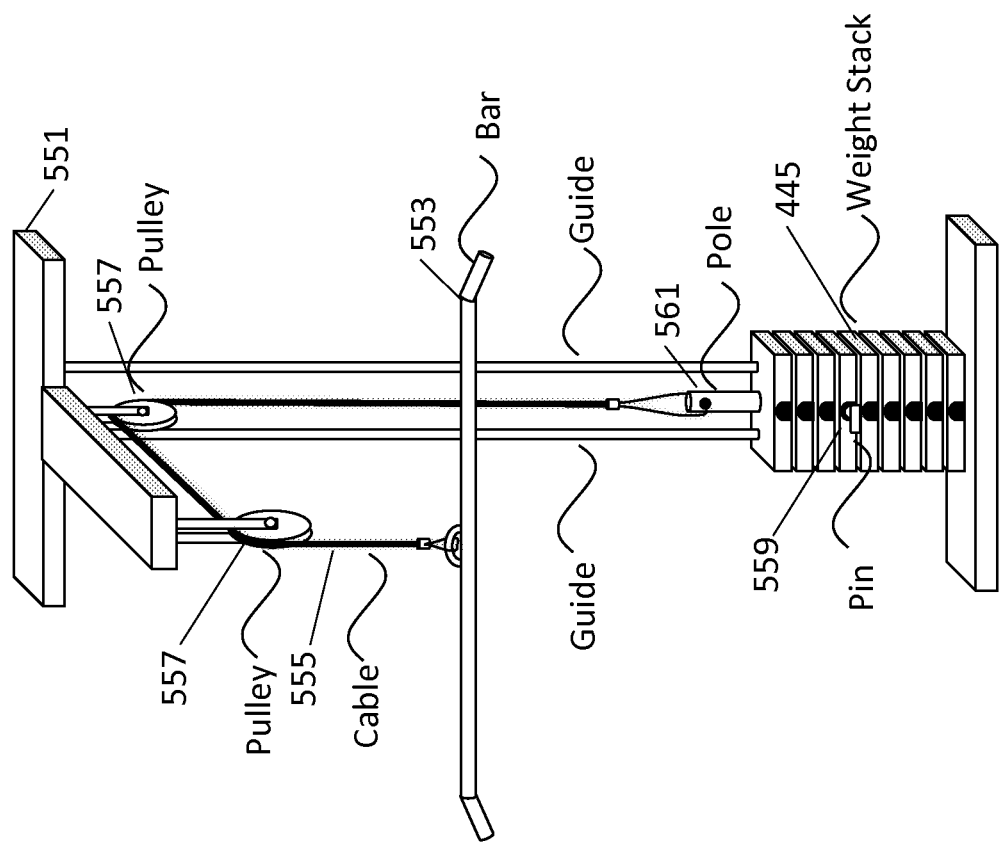

FIGS. 4a and 4b illustrate a perspective view of a pulley based exercise machine.

Figure 4C:
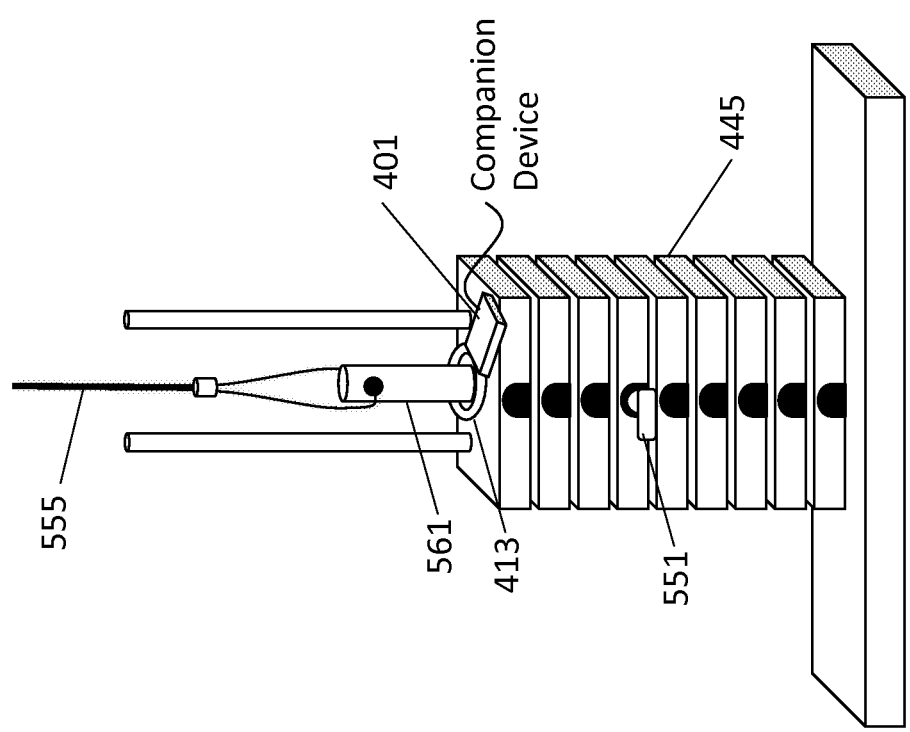

FIG. 4c illustrates a view of a companion device placed on the weights portion of the pulley based exercise machine.

Figure 5B:
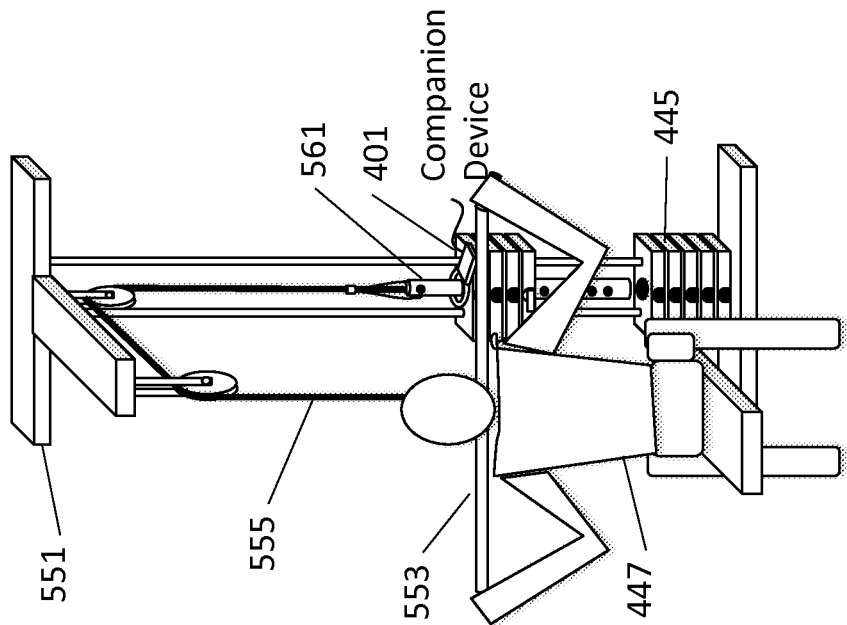
Figure 5A:
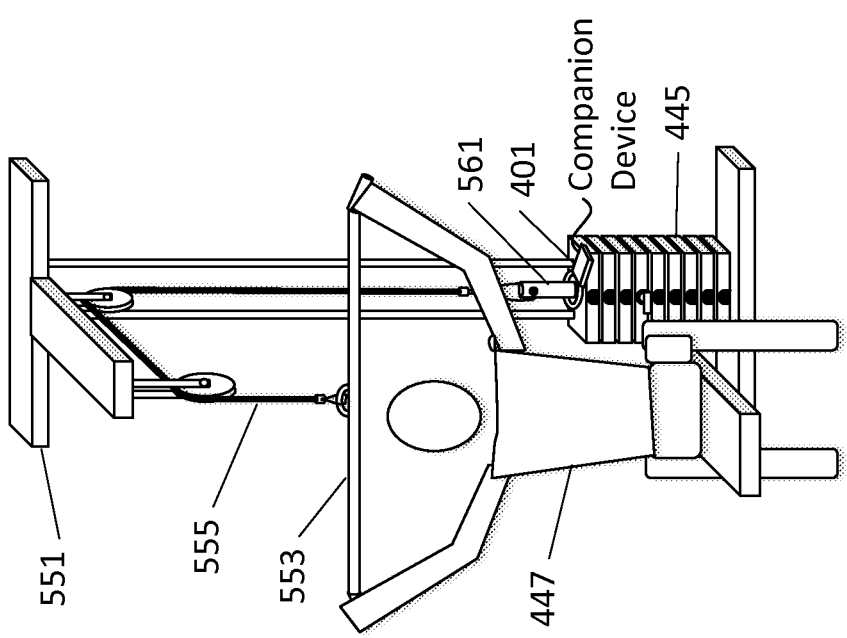

FIGS. 5a and 5b illustrates a user using a pulley based exercise machine.

Figures 6A, 6B, 6C:
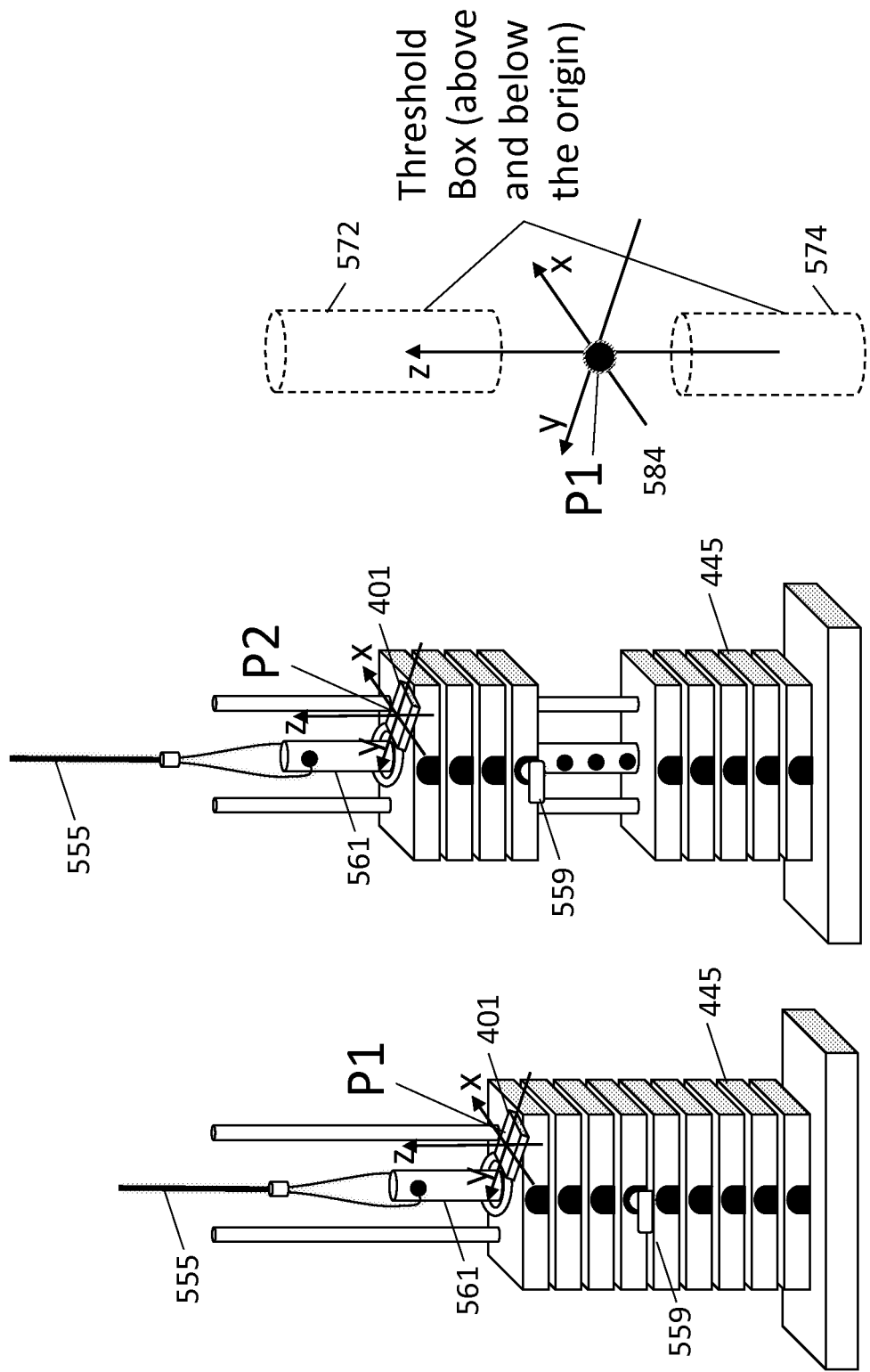

FIGS. 6a and 6b illustrate a view of a companion device placed on the weights portion of the pulley based exercise machine.

FIG. 6c illustrates threshold boxes for use with the companion device.

FIG. 7a illustrates a sequence of user movements on a pulley based exercise machine.

FIG. 7b illustrates a graphical output of sensor data from the wearable device on the core during the sequence of user movements on a pulley based exercise machine.

FIG. 7c illustrates a graphical output of sensor data from the companion device on the core during the sequence of user movements on a pulley based exercise machine.

FIG. 7d illustrates the assessed likely user actions during the sequence of user movements on a pulley based exercise machine.

FIG. 8a illustrates a graphical representation of user actions over a period of time.

FIGS. 8b and 8c illustrate evaluation options associated with user actions over a period of time.

FIGS. 9a and 9b illustrate a user on a bench press with a companion device coupled to the weights.

Figure 10C:
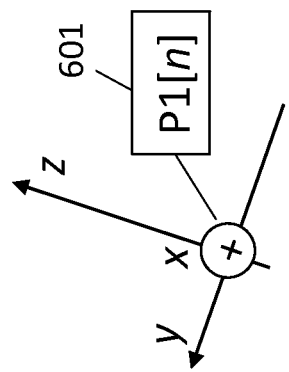
Figure 10B:
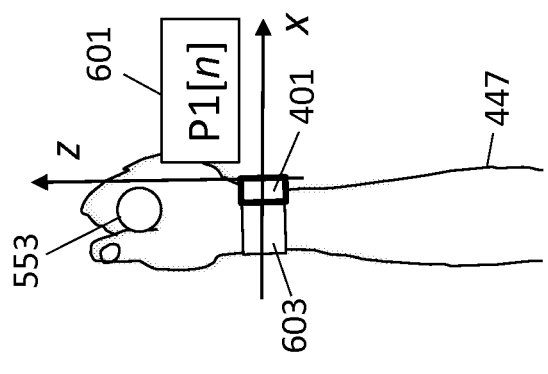
Figure 10A:
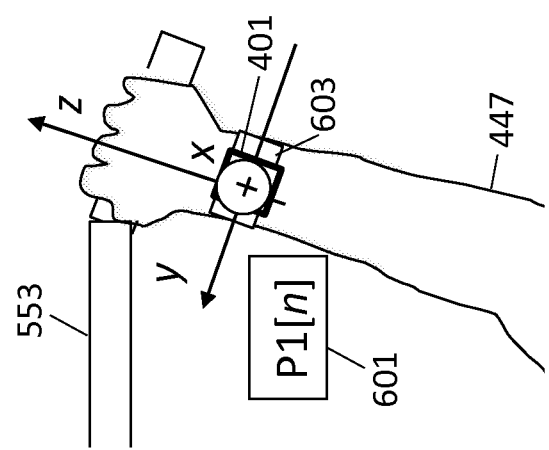

FIGS. 10a and 10b illustrate a smart watch used as a companion device during user movements on a pulley based exercise machine.

FIG. 10c illustrates the position and orientation of the companion device in a XYZ coordinate system.

Figure 11B:
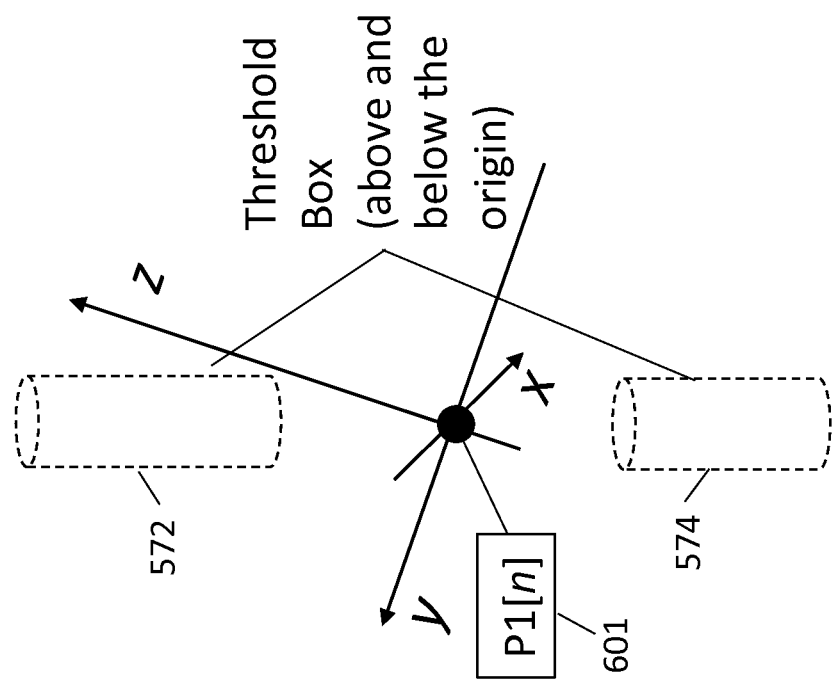
Figure 11A:
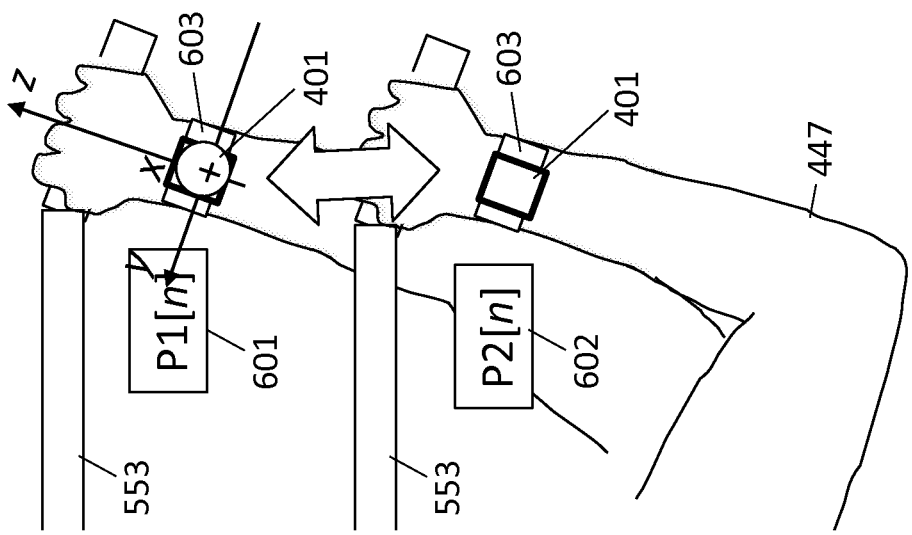

FIG. 11a illustrates a smart watch used as a companion device during user movements on a pulley based exercise machine.

FIG. 11b illustrates an embodiment of threshold boxes used to identify QMs during user movements on a pulley based exercise machine.

Figure 12B:
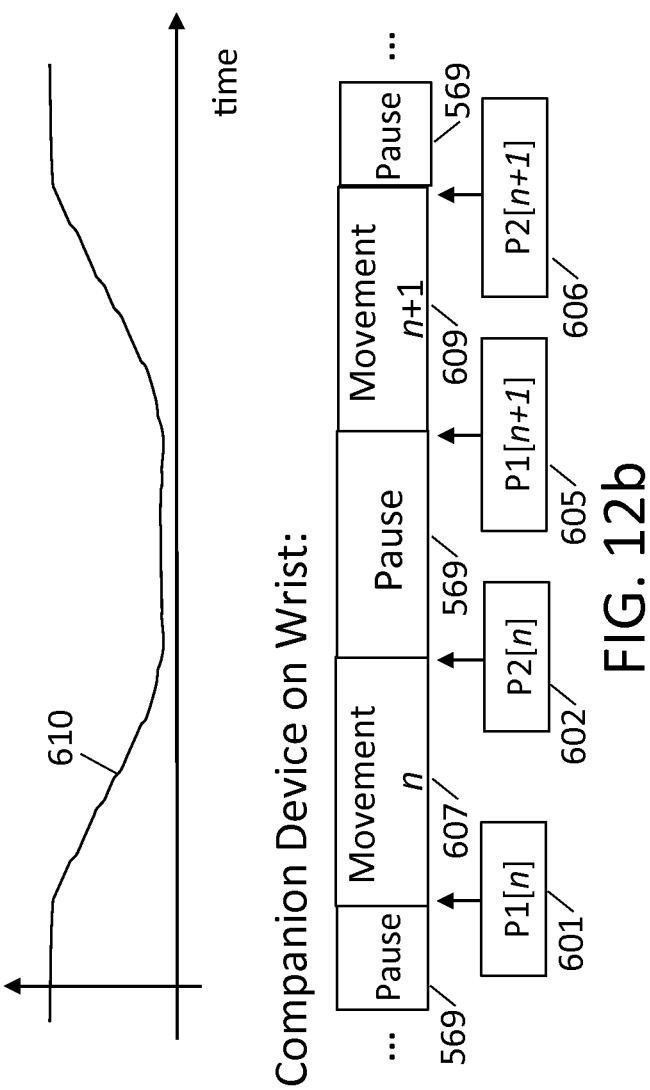
Figure 12C:
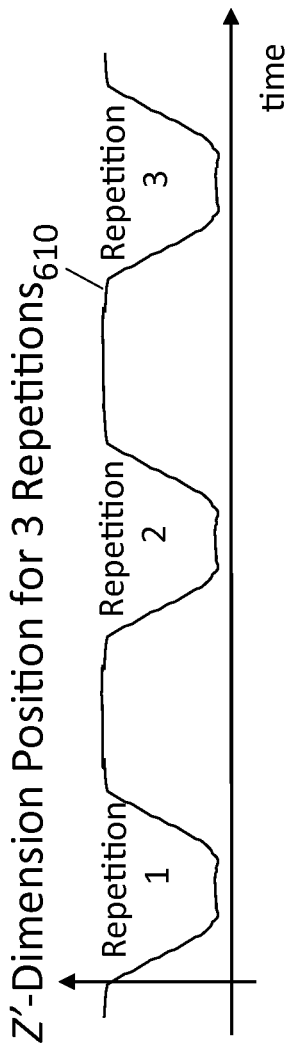
Figure 12A:
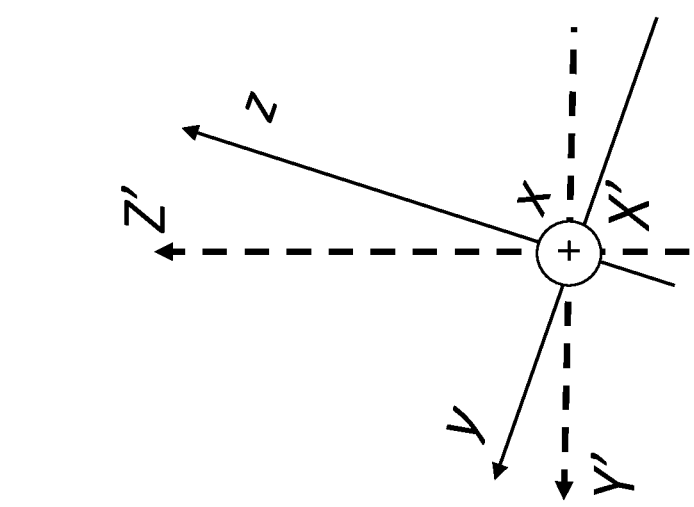

FIG. 12a, a X'Y'Z' coordinate system for a companion device.

FIG. 12b illustrates a graphical representation of a Z' position, pauses and movements over time.

FIG. 12c illustrates a graphical representation of a Z' position for a companion device during multiple repetitions over time.

FIGS. 13a, 13b 13c and 13d illustrate embodiments of flow charts of body movement and core activity data processing.

Figure 14:
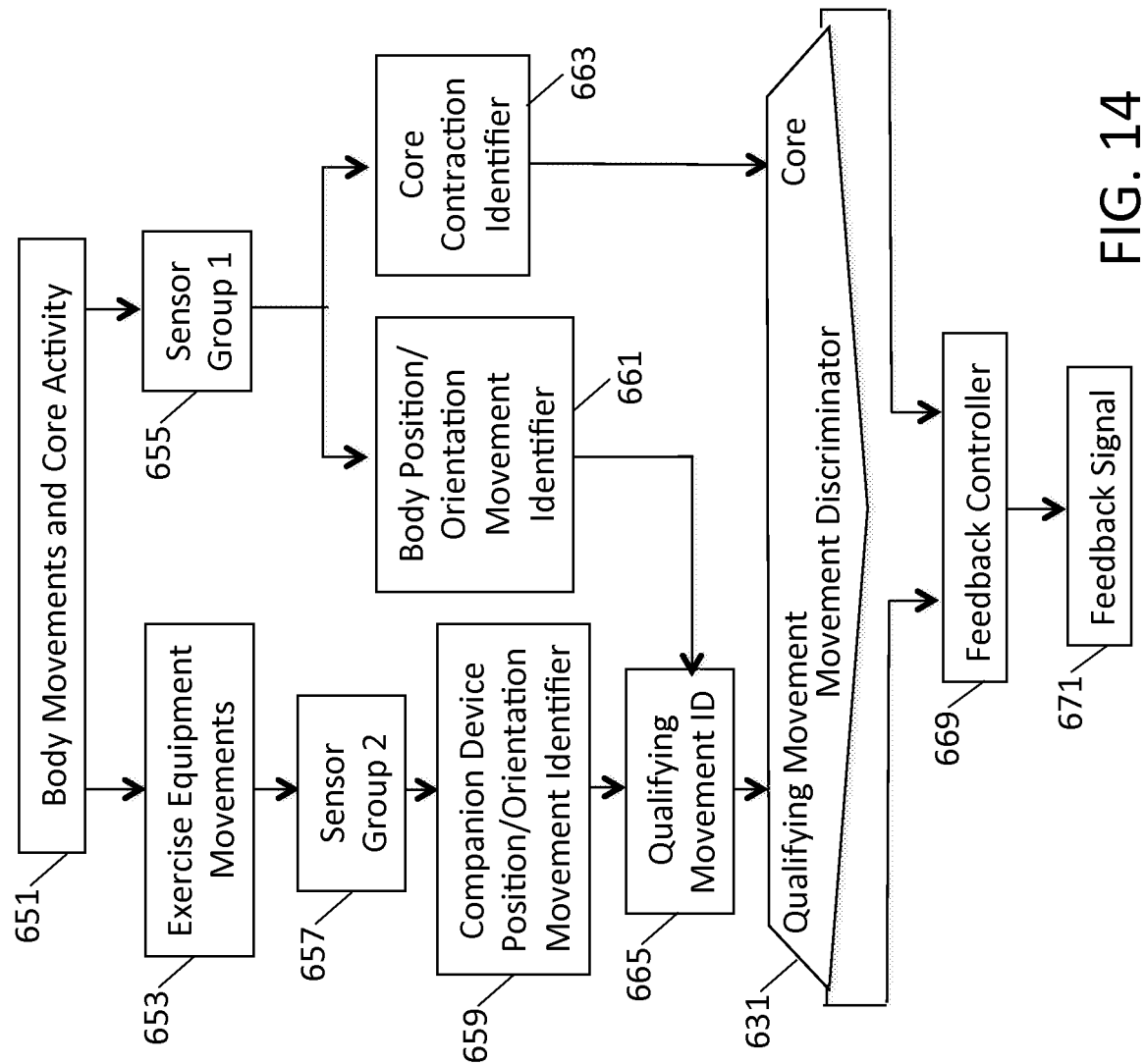

FIG. 14 illustrates a flow chart of body movement and core activity data processing.

Figures 15A, 15B:
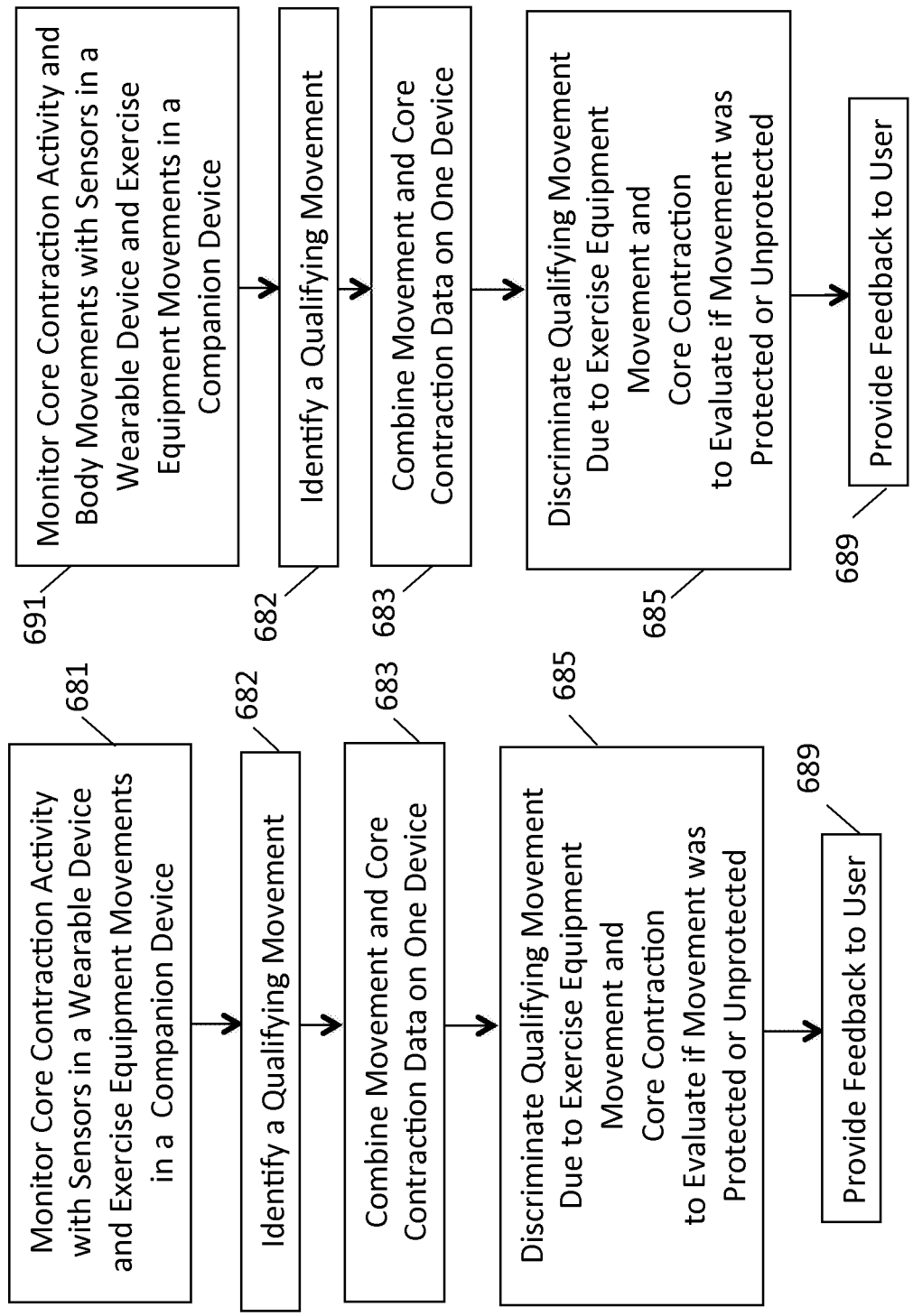
Figure 15C:
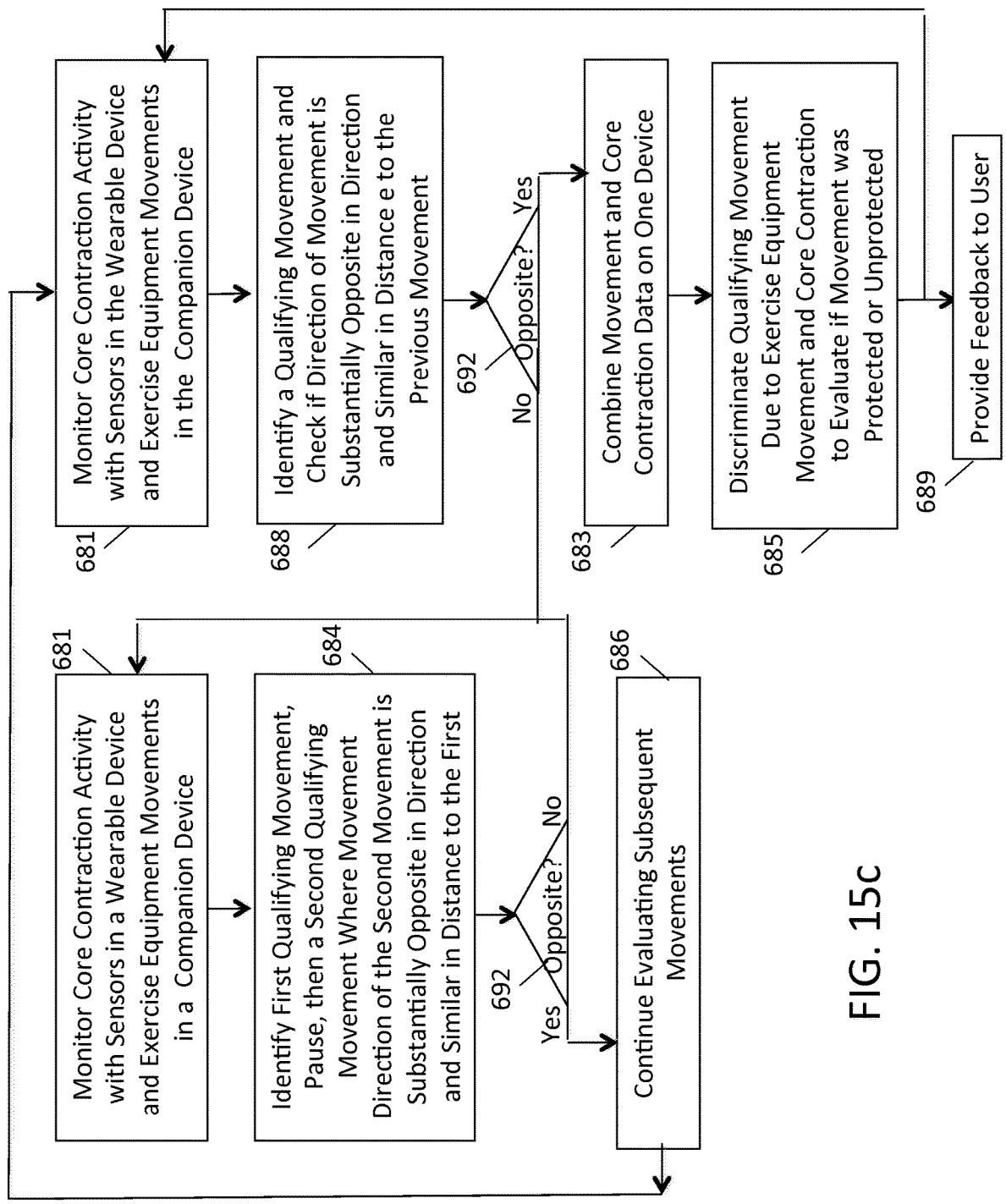

FIGS. 15a, 15b and 15c illustrate embodiments of flow charts for identifying protected/unprotected qualifying movements and providing user feedback.

DETAILED DESCRIPTION

In U.S. patent application Ser. No. 14/132,808, an inventive device and system are described which enable real time tracking of the inner core muscles. The device described in U.S. patent application Ser. No. 14/132,808 that may be worn on a belt in a location between the naval and the crotch (or above or around the naval as may be preferred in some applications) can be known as a "wearable device" or "wearable". In the present application, an inventive device is described which can operate in an inventive system as a companion device to the wearable device.

The inventive companion device may communicate directly with the wearable device. The companion device may also communicate with a computer which may be a portable computer or a portable computing device that includes a means of communicating with the wearable device and the companion device. Examples of a portable computing device may include a smart phone, smart pad, laptop, PC, or a dedicated device containing appropriate elements.

A block representation of the companion device 401 is shown in FIG. 1a. The manner in which the companion device 401 is packaged may vary and can be suited to meet the requirements of different applications. The basic elements of the companion device 401 are: a. a printed circuit board (PCB) 403—containing sensors such as accelerometers and gyros, integrated circuits and including one or more microprocessors, memory, communications protocol device to support USB and/or a wireless communications protocol device such as Bluetooth, Zigbee, WiFi or other which can be electronic components 405 all mounted on the PCB 403; b. Battery 407—may be a rechargeable or replaceable battery; and c. Package 409—a housing to hold the PCB 403 and battery 407 together.

The companion device 401 may be connected to a person or an object, depending on the application. In order to connect the package 409 to a person or an object, an attachment device including a means to hold or house the package and a means to attach to a person or object may be utilized. In most applications, the companion device 401 may include a PCB 403, battery 407, package 409, and attachment device. In some applications, the package 409 and attachment device may be combined.

A package 409 may be designed to connect or attach to two or more attachment devices to enable a single package 409 containing a PCB 403 and battery 407 to be used in different applications. This configuration of multiple attachment devices that can be interchangeable may be attractive to a user who may purchase one package 409 and one or more attachment devices. Examples of attachment devices are shown in FIG. 1b-FIG. 1i. Each of the attachment devices 411 is shown holding or housing a package 409 containing a PCB 403 and a battery 407. In FIG. 1b, an attachment device 411 with a gapped ring 413 structure is shown. This gapped ring 413 may be pliable, re-shapeable, or bendable, allowing the gap 415 to widen when pressure is applied and narrow when pressure is removed. It may be made from different materials or combinations of materials including plastic, rubber and wire. The design may facilitate creating a temporary attachment of the device to exercise equipment or other object. For example, the gap 415 may widen when the gap 415 is placed against a pole or bar, and the gap 415 may narrow around the pole or bar once the pole or bar is enclosed by the gapped ring. Alternatively, the gapped ring 413 may hook onto a cable. The weight of the companion device 401 pulling against the gapped ring 413 wrapped around the pole, bar, or cable may hold the companion device 401 in temporary fixed location. The gap 415 in the gapped ring 413 may be situated and sized to facilitate attachment and removal to and from, while allowing a sufficiently effective attachment to the object while connected.

In FIG. 1c, the attachment device is a strap 417, which allows the package 409 to connect to a user's wrist or leg or other part of the body. An embodiment of the companion device in this strap 417 configuration is a smart watch. The ends of the strap 417 may be closed around the user using many methods including those used to attach watches or other bands around a wrist, Velcro, or other suitable attachment methods. In FIG. 1d, the attachment device 411 contains a hook 419, and in FIG. 1e, the attachment device 411 contains a ring 421 with a latched arm 423, both of which may be used to connect to exercise equipment or other object similar to the gapped ring 413 of FIG. 1b. In FIG. 1f, the gapped ring 413 is again repeated, but in this this embodiment, the gapped ring 413 may be a bendable and soft, yet firm material like rubber, and with teeth that may grip onto a pole and resist rotation once connected around a pole.

In FIG. 1g, the attachment device 411 contains a magnet 429, allowing the companion device 401 to be connected to ferromagnetic metal objects 427 including exercise equipment 425. In FIG. 1h, the attachment device 411 includes a specific connector A 431 designed to attach to and detach from another specific connector B 433 which may attach to exercise equipment 425 or other objects. Finally, in FIG. 1i, a carrier to hold a smart watch configuration of the companion device is shown with a gapped ring 413. The gapped ring 413 is an example of a connecting element that may be attached to the carrier to attach the smart watch to the exercise equipment 425. Design elements such as shape, weight, and materials may be combined appropriately to achieve product objectives including ease of attaching and detaching, stability including minimal movement when attached, robustness to dropping, comfort for handling, and facilitating sensor measurements of target movements for the intended application.

The companion device 401 may be attached to exercise equipment what may be referred to as the equipment-attached configuration. Similarly, the companion device 401 may be attached to the user in what may be referred to as the user-attached configuration. In an embodiment, companion device 401 may be attached to the user's wrist.

With reference to FIG. 2, a block diagram of an embodiment of the companion device 401 is illustrated. The 3-axis accelerometer 103 and the 3-axis gyroscope 105 are coupled to the processor 321. The processor 321 can include a qualifying movement algorithm 324 and a protected qualifying movement algorithm 325 which can be software stored in a memory 339 or firmware. Movement signals from the 3-axis accelerometer 103 and the 3-axis gyroscope 105 can be processed by the qualifying movement algorithm 324. During a user's repetition of an exercise, the companion device 401 may move approximately the same distance as the user's 447 body moving the user interface 441. The qualifying movement algorithm used in wearable device 449 to identify body movements that are qualifying movements may be used in the companion device 401 in an exercise equipment-attached configuration to identify qualifying movements based on exercise equipment movements. Similarly, the qualifying movement algorithm used in wearable device 449 to identify body movements that are qualifying movements may be used in the companion device 401 in a user-attached configuration to identify qualifying movements based on movements of the user's body, for example the user's arms or legs.

Thresholds used for QM identification may be adjusted depending on factors such as the specific exercise and design of the exercise equipment when using the qualifying movement algorithm on the companion device 401. These movement thresholds for QM ID may be modified using display 448 and item selector 444. Signals from the qualifying movement algorithm 324 and signals from the core contraction sensor on the wearable 449 can be processed by the protected qualifying movement algorithm 323 which may determine whether a movement is protected or unprotected.

In an embodiment, the qualifying movement algorithm 323 and the protected qualifying movement algorithm 325 can be updated as improvements or changes are made to these algorithms 323, 325. In an embodiment, the algorithm updates can be transmitted to the companion device through the communications 331 port which can provide network communications with other computing devices. The processor 321 can communicate through communication device 331 to the processor on the wearable, to output through various output devices on the wearable information to the user through one or more of: a buzzer, a sound generator, a transcutaneous electrical nerve stimulator (TENS) zapper or other output device(s). The output devices can emit output signals to the user indicating correct core contractions during QMs or incorrect core contractions. In another embodiment, information may be provided to the user through one or more output device on the companion device. The output devices on the companion device may be similar to the output devices that may be on the wearable device with the addition of the display 448.

The communications device 331 can be a Bluetooth device that provides wireless communications to other devices. A battery 333 can be coupled to a power management module 335 which can control the distribution of electrical power to the system components. The battery 333 can be rechargeable and capable of being charged with a charger. The processor 321 can also be coupled to a memory 339 which can store information about the user(s) and record user movement and core contraction data. The system can also include a clock reference 337 which can provide a system reference clock to the processor which may also be used to derive sampling clocks for the sensors 103, 105. If the system has a minimum of intermittent access to date and time information, for example through a cellular system, the clock reference 337 may be utilized in an algorithm using such date and time information so that recorded movements and core contractions can be stored with time stamps. A display 448 can be used to display settings, options, or parameters. Item selector 444 can be used to select options or modify parameters shown on display 448. In some applications, additional sensors such as magnetometers and temperature sensors may be included to improve the quality of movement sensing and identification.

A simplified block diagram illustrating the companion device 401, exercise equipment 425 and wearable device 449 is shown in FIG. 3a. In this example, the companion device 401 is utilized by a user 447 with exercise equipment 425. The user 447 can be coupled to the wearable device 449 and in direct contact with the exercise equipment 425. The exercise equipment 425 can include: a. User Interface 441 which can be an object that the user 447 interfaces with in order to execute the intended exercise; the user interface 441 may be a pole, bar, or handles that may be fitted with appropriate padding to interact with the user's hands, arms, legs, feet, neck, torso, back, or other body parts or combinations of body parts involved in the exercise; b Weights or Weight Stack 445 which can be a stack or discs of metal, cement, or other high density material that provides resistance to the user's muscles; Generally, the amount of weight 445 may be adjustable. Some exercise equipment 425 may utilize other means to provide resistance to the user's muscle movements s such as rubber bands or elastic bands. Other exercise equipment 425 may be configured to utilize the user's body weight to provide resistance for the user's muscles; and c. Movable Element 443 which can couple the user interface 441 of the exercise equipment 425 to the weight stack 445 and moves during the exercise with the user interface 441 and the weight stack 445. Examples of the moveable element 443 may include cables which may connect the user interface 441 to the weight stack 445, poles that the weight stack 445 may attach to, and pulleys that guide the user interface 441 to the weight stack 445. In some cases, the Moveable Element 443 may not be present and the user interface 441 may connect directly to the weights 445.

In FIG. 3a, the attachment device 411 of the companion device 401 is coupled to the moveable element 443 and the movement sensors 407 detect the movements of the movable element 443. In FIG. 3b, the attachment device 411 of the companion device 401 is coupled to the user interface 441. The attachment device 411 of the companion device 401 may be coupled to any element of the exercise equipment 425 that moves in response to the user 447 performing movements of the exercise. In some embodiments of the attachment device 411, the companion device 401 may be coupled directly to the user 447 as shown in FIG. 3c. In this configuration, the inventive system may be utilized for applications other than interfacing with exercise equipment.

In FIG. 3d, a depiction of a user 447 wearing an embodiment of a wearable device 449 on a belt strap near the waist and an embodiment of a companion device 401 on the wrist is shown. In applications shown in FIGS. 3c and 3d, the user 447 may interface with the exercise equipment. In addition, the user may interface to athletic equipment, objects and human subjects encountered in occupations involving lifting, and other devices and elements involving lifting.

In U.S. patent application Ser. Nos. 14/789,136 and 62/019,522, a user's body movements are monitored for qualifying movements by movement sensors on the wearable 449 and the user's core is monitored by a core contraction sensor on the wearable 449. The present application addresses a problem that may arise with using movement sensors on the wearable while performing exercises on many exercise machines and many pieces of exercise equipment. In many exercise movements performed on exercise equipment and machines, the user's torso may not move while performing exercises. For these movements, the companion device 401 is introduced to be placed on parts of the exercise equipment that move during the exercise in the equipment-attached configuration or parts of a user 447 such as the user's wrist in the user-attached configuration. These exercise movements may be detected by the movement sensors in the companion device 401. The user's core may be monitored during the exercise movement by the core contraction sensor on the wearable 449.

Exercise movements on the exercise machines and exercise equipment may be considered qualifying movements. The discrimination function, determining if the movement is a protected qualifying movement or unprotected qualifying movement may be performed in the processor on either the companion device or the wearable device. In one embodiment with reference to FIG. 2, discrimination is performed on the companion device by the Protected Qualifying Movement Algorithm 325 running on processor 321 and the core sensor data is transferred from the wearable 449 through the communication device 331 on the wearable 449 to the communication device 331 on the companion device 401. Feedback to the user 447 may be provided from an output device on either the companion device 401 or the wearable device 449. In an embodiment, feedback is provided when a qualifying movement is identified as unprotected through a buzzer on the wearable device 449. The result from the Protected Qualifying Movement Algorithm 325 may be transferred through the communication device 331 to the communication device 331 on the wearable 449 where the buzzer may provide a buzz to the user 447 indicating an unprotected movement.

In an embodiment, Bluetooth 4.0 (or BLE—Bluetooth Low Energy) can be a communication protocol utilized for the communication blocks 331 shown in FIGS. 3a-3c. In BLE, one side of the communication link is the master and the other is the slave. In an embodiment utilizing BLE as the communication protocol, the companion device 401 is the master and the wearable 449 is the slave. In another embodiment, when BLE is utilized and the wearable 449 is paired with a smart phone or a smart device with BLE, the smart phone may be the master and the wearable 449 may be the slave. The smart phone or smart device is a convenient master since it has a built in display and an item selector which enables the user to select and unselect items. This facilitates pairing and unpairing BLE devices since the display can show which BLE devices are being advertised during pairing to enable a specific wearable to be selected for pairing, and for unpairing when needed. An instance in which unpairing is needed may include when the master is changed from the smart device to the companion device 401. In embodiments utilizing BLE, a display 448 and item selector 444 may be included on the companion device 401 to facilitate pairing with a specific wearable 449. Without display 448 and item selector 444, it may be difficult to control which BLE device the companion device 401 pairs to. In BLE, unpaired slave devices advertise by sending out identifying data for itself. A master device may generate a list of unpaired slave devices to enable the user 447 to select which slave device to pair with. Display 448 may enable a user to view a list of unpaired slave devices and item selector 444 may enable a user to select a slave for pairing. Display 448 and item selector 444 may also be used to enable a user to unpair the wearable 447 and the companion device 401.

There are a number of types of equipment used in most gyms or exercise facilities. Exercise equipment can include: a. Pulley based exercise machines 551, an example of which is shown in FIGS. 3a-3b; b. Free weights, including dumb bells, barbells, kettle bells and weight balls; and c. Rubber bands and elastic bands. Embodiments of the inventive system may be utilized with each of these types of equipment.

In U.S. patent application Ser. Nos. 14/789,136 and 62/019,522, comprehensive strategies for identifying Qualifying Movements in every day activities based on data from sensors are described. In one embodiment, data from the wearable device is processed to identify pauses and movements between pauses. When the duration of a movement is within a programmable set of limits, that movement is further evaluated for identification as a Qualifying Movement. In one embodiment, this further evaluation comprises identifying a reference position and orientation at the start of Movement n referred to as P1[n], and identifying a second position and orientation at the end of Movement n referred to as P2[n]. The difference between P2[n] and P1[n] is the change in location or the distance and direction moved, and the change in orientation or the rotation over the course of the movement. Based upon these changes in position and orientation exceeding minimum thresholds indicating a movement and not a pause, signal processing modules may evaluate the movement in order to identify the movement as a Qualifying Movement or not a Qualifying Movement. For applications in which the companion device 401 is placed on exercise equipment or other devices, the thresholds may be a function of parameters that may include the distance user interface 441 or movable element 443 on exercise equipment 425 travels during a movement of the exercise with a specific user 447. For applications in which the companion device 401 is worn on the user 447, the thresholds may be a function of parameters that may include the distance the user's body that the companion device 401 is attached to travels during a movement of the exercise.

Let us examine a specific example of how the companion device may be used in an application with an exercise machine and how the algorithms for Qualifying Movement Identification described in U.S. patent application Ser. Nos. 14/789,136 and 62/019,522 may be extended to applications with the companion device. The companion device may provide additional data to identify Qualifying Movements not otherwise identifiable with data from the wearable device alone. For example, during a pull-down movement when performing the lat pull-down exercise, the wearable device may only detect small amounts of movement making identification of a Qualifying Movement based only on data from the wearable device very difficult. However, movement of the companion device may be significant and combined with data available from the wearable device, may enable the system to perform identification of a Qualifying Movement. Since the companion device may be used in different applications states, it may be preferable when using the companion device to program both the companion device and the wearable device for the same application state to facilitate efficient and effective use of the available data. An example of an application state is Gym Exercise. In an embodiment of Gym Exercise, the movement sensors on the wearable may also be used to identify body movements. In an embodiment using the movement sensors on the wearable, undesired movements such as rocking the torso during the exercise may be identified and feedback may be provided to the user.

A pulley based exercise machine 551 configured for a user to perform an exercise often referred to as lat pull-down is shown in FIG. 4a and FIG. 4b. The machine 551 is shown configured with a wide bar 553 connected to a cable 555 that connects through two pulleys 557 to an adjustable stack of weights 445. The amount of weight 445 to be used during the exercise may be selected with a pin 559 that groups a selected amount of weight 445 to be applied to a slotted bar 561 which the pin 559 connects into, and connects the weight 445 to the cable 555, and ultimately to the wide bar 553. As the bar 553 is pulled in the downward direction as shown in FIG. 3b, the group of selected weights 445 from the weight stack 445 is lifted upward. The weight from the selected weight stack 445 through the pulley system creates a load to the user performing the exercise.

In FIG. 4c, an embodiment of the companion device 401 utilizing a gapped ring 413 is shown with the gapped ring 413 placed on the slotted bar 561. The starting position of a user 447 performing the exercise is depicted in FIG. 5a. As the user 447 pulls the bar 553 downward, the companion device 401 moves upward with the selected group of weights 445 as depicted in FIG. 5b. The position of the selected weights and the position of the companion device 401 just prior to the user 447 pulling down the bar 553 are shown in FIG. 6a. This position of companion device 401 is P1 for the current exercise movement. After the user pulls the bar 553 downward and the selected group of weights 445 moves upward, the companion device 401 is in position P2 for the current exercise movement as shown in FIG. 6b.

An example of the Threshold Box for the movement of companion device 401 is shown in FIG. 6c as two cylindrical volumes 572, 574 above and below the origin. Threshold Boxes may be defined as a cylindrical volume 572 above and a cylindrical volume 574 below P1 to enable either an upward movement or a downward movement of the companion device 401 to be identified as a qualifying movement. If the Exercise Movement Algorithm evaluates that position P2 is enclosed by the Threshold Box, a QM is identified and the Protected Qualifying Movement Algorithm 325 may be performed. The top of the Threshold Box cylindrical volume 572 may extend arbitrarily high in the upward direction and the bottom of the Threshold Box cylindrical volume 574 may extend arbitrarily low in the downward direction.

FIG. 7 illustrates a sequence of user movements and the sensor data from the wearable device and the companion device detected during the user movements. The data from wearable device and the companion device may be used together to identify Qualifying Movements during lat pull-downs on the exercise machine 551. In FIG. 7a, the sequence of user 447 movements moves from left to right with time. The user 447 begins in the release-up position (in the first user illustration), moving to the position of pull-down 563, pausing, then from the position of pull-down moving back to the position of release-up 565. Note that the pauses are located at the start, between the release-up-to-pull-down 563 and pull-down-to-release-up 565, and finally at the end. Breaking the movement into steps as demonstrated in this example encourages the user movements such as these to be deliberate and carefully executed. Further, it may facilitate encouraging the use of the core during the movements.

In an embodiment, the system can identify QMs by first assessing Movement n. Based on prior movements, which can be the user moving to the exercise machine 551 from a standing position and sitting on the exercise machine 551, the algorithms may assess that the user's state is sitting. Other examples of possible user states may include: standing, sitting, lying, and riding transportation. As shown from the sensor data from the wearable device 567 in FIG. 7b, no appreciable movement is detected by the sensors and pauses 569 are detected throughout the illustrated exercise repetition from the wearable device sensors. The sensor data 571 from the companion device 401 shown in FIG. 7c is therefore critical in this example for identifying pauses and movements. Since the companion device 401 moves in direct response to the movements of the user 447 performing the exercise, sensor data 571 from the companion device 401 may be used to detect such movements.

Referring to the user movements shown in FIG. 7a, prior to the user performing the pull-down movement 563, the user 447 pauses. This is detected by the companion device 401 sensors as a pause. Following this, is a movement of the companion device 401 upwards in response to the pull-down movement 563 of the bar 553. This is followed by another pause. The movement resulting from the pull-down movement 563 of the bar 553 can be labeled Movement n. Utilizing Position Thresholding, the change in companion device's 401 position and orientation from P1 to P2 during the movement may be evaluated for QM ID. Suppose a Threshold Box is defined as shown in FIG. 6c as cylindrical volumes 572, 574 with diameter 5 inches and located 6 inches above and below P1. Further suppose for example, the change in position from P1 to P2 is a substantially vertical change of 15 inches upwards. This would place P2 in the Threshold Box cylindrical volumes 572, 574 and a qualifying movement would be identified.

The algorithm assessment of likely user actions is shown in FIG. 7d. Since the system is in application state for Gym Exercise, the user state is assumed to be sitting, the wearable device is detecting a user pause, and an upward movement is detected by the companion device 401 meeting the requirements of a QM, user Movement n may be identified as one direction of an exercise movement or repetition (rep). Further suppose the change from P1 to P2 during Movement n+1 is a substantially vertical change of 15 inches downward. Using the same definition for the Threshold Box cylindrical volumes 572, 574 P2 can be contained in the Threshold Box and Movement n+1 may be identified as qualifying movement. In applications in which movement polarity is tracked, the directions of the exercise repetitions may be identified. In some embodiments, the assumption of the user's state may be beneficial while in other embodiments the user's state may not be beneficial. In the current example where the Threshold Box can be defined both above and below location P1, information regarding the user's state may not be beneficial.

There are a number of ways the system controller, which may be a software or firmware function controlling the algorithms, may respond to this scenario. One exemplary embodiment will be investigated in greater detail. Let us assume the system is programmed to be configured for the Gym Exercise application state including the wearable device and the companion device. This application state may provide context to allow combinations of sensor data from both the wearable device and the companion device to be advantageously utilized. A large number of exercises, when performed properly on exercise machines may result in only a small movement of the torso region of the body in order to isolate specific muscles involved with the exercise. Therefore, the QM ID of one repetition of an exercise may be comprised of a pause detected by the sensors on the wearable device together with a pause followed by a movement detected by sensors on the companion device in one direction and a certain distance movement of the companion device resulting from a first user movement during the exercise, followed by a pause, then followed by a movement detected by sensors on the companion device in substantially the opposite direction and similar in companion device distance movement resulting from a second user movement during the exercise. In many exercises, the first and second movements of the exercise may be substantially opposite movements.

If the movement of the companion device in the vertical dimension upwards places P2 in the Threshold Box cylindrical volumes 572, 574, and there is coincidently little torso movement detected by the wearable device during the same time period, a QM may be identified corresponding to an exercise movement on a machine. Since P2 is enclosed by Threshold Box 572, the movement of the weight stack was upwards. The Threshold Box may be a function of the user's body characteristics such as height, shoulder width, or arm length and exercise equipment used, and may be established or defined beforehand or adjusted prior to an exercise.

Typically, a number of repetitions are performed to comprise one set of an exercise. For example, a person may perform 10 repetitions of the exercise in succession and refer to the 10 repetitions as one set. Further, it is common to perform multiple sets of the exercise. For example, between one and four sets of one exercise may be performed during a workout session. These sets may be performed with rest in between, or alternated with other exercises.

In others embodiments, the system may be designed to evaluate the first repetition of the exercise but not report a QM, but instead use the first repetition of an exercise for data gathering and identifying the start of a pattern. Then, on the second and subsequent repetitions, the available data including the user's state, application state (Gym Exercise mode), user's torso movements, and P1 to P2 movement data of both the first and second movements (of a two movement exercise) may be used to identify a QM. This is an example of utilizing additional data. Utilizing additional data may result in a system that is less susceptible to making incorrect positive QM IDs.

In some communication protocols governing device to device communications, one device performs the role of a master and the other the role of a slave from a protocol perspective. Depending on the application and the details of the protocol, there may be preferred assignment of the roles of master and slave. As described earlier, in most applications of the inventive system operating with a wearable device and a companion device employing BLE, the companion device may be the master from a communications protocol perspective and the wearable device may be the slave. In some applications, it may be preferred that the wearable device be the master and the companion device be the slave.

The functions required in the system comprising a wearable device and a companion device include: a. inferring exercise movement by identifying equipment or body movement, for example wrist movement and evaluating the movement as a qualifying movement; b. identifying core contraction status; c. discriminating the movement as a protected or unprotected qualifying movement; and d. providing feedback to the user. In some cases, torso movement data may also be used to identify a qualifying movement or an unwanted movement such as excessive rocking of the body during an exercise movement. In some applications, feedback may be provided to the user when the user performs an unwanted movement(s).

Since the discriminating function requires a time alignment evaluation of movements and core contractions, some system embodiments may have the devices establish time synchronization in order that time stamps may be used. Time synchronization may allow time stamps to have a common meaning to the devices in the system so that the detected timing of the sensor data from the different devices can be accurately recorded and compared. In another embodiment, sensor data may be passed in real time with low latency from one device to another. If latency in acquiring sensor data on a second device and transmitting the data to a first device is low enough, the sensor data from the second device may be processed by the processor on the first device as though the sensor on the second device is virtually on the first device and time stamps may not be necessary. Calibration and other techniques may be used to time align data taken on separate devices.

In most applications, the companion device 401 may monitor movement of the exercise machine or equipment 425 and the wearable device 449 may monitor the user's core contraction status. Discriminating the movement may occur on the wearable device 449, the companion device 401, or an additional device such as a PC, smart device, or dedicated device (external device). In most applications of the inventive system, each of the wearable device 449 and companion device 401 will have a processor 321 capable of running the Protected Qualifying Movement Algorithm 325 to determine or predict whether the detected movements are protected or unprotected movements. Since both the timing of the exercise movement or qualifying movement and the timing of the core contraction status are needed to discriminate the movement, the data must be sent through the communication devices 331 to the device performing the discrimination.

In an embodiment, the Protected Qualifying Movement Algorithm 325 may run on the processor 321 residing in the companion device 401. In this embodiment, the wearable device 447 may transmit the core contraction status data through the communication devices 331 to the companion device 401. In another embodiment, the Protected Qualifying Movement Algorithm 325 may run on the processor 321 residing in the wearable device 449. In this embodiment, the companion device 401 may communicate through the communication devices 331 data associated with the qualifying movement identification including timing features of the relevant data. An example of a timing feature of a qualifying movement may include a time stamp near or at the start of a qualifying movement.

In another embodiment, the Protected Qualifying Movement Algorithm 325 may run on the processor residing on an external device such as a smart device, PC, or dedicated device in which case both the qualifying movement data and core contraction status and relevant timing information may communicated through the communication devices 331. Feedback to the user 447 may be provided through the wearable device 449, the companion device 401, an external device, or a dedicated feedback device. Various forms of feedback are possible. Depending on the nature of the feedback, a specific type of the feedback device may be preferred. The device on which the Protected Qualifying Movement Algorithm 325 may communicate through the communication devices to the device providing feedback. In different embodiments, feedback may be provided by more than one feedback device. In another embodiment, feedback associated with a protected or unprotected movement may be provided at different times. For example, an unprotected movement may result in substantially immediate feedback through the buzzer feedback device on the wearable device 449. A record of the unprotected movement may be stored in memory and reported to the user at a later time in the form of a data table or as part of a Core Score. In an embodiment, the feedback for an unprotected movement may be through a buzzer on the wearable device 449. In this embodiment, if the Protected Qualifying Movement Algorithm 325 is run on a processor 321 residing on the companion device 401, the companion device 401 may send a signal through the communication devices 331 to the wearable device 449 that an unprotected movement has been identified. In another embodiment, the companion device 401 may send a signal through the communication devices 331 to the wearable device 449 which can cause the feedback device to buzz, to buzz with a specific pattern, or to buzz with a specific time duration. In an embodiment, the Protected Qualifying Movement Algorithm 325 is run on a processor 331 residing on the wearable device 449 and the processor 331 may communicate directly with the buzzer. In an embodiment, the Protected Qualifying Movement Algorithm 325 is run on a processor 321 residing on an external device and it may communicate to the wearable device 449 to cause the feedback device to buzz appropriately to inform the user 447 of an unprotected qualifying movement.

As just described, the signal processing for identifying protected and unprotected movements may be distributed among the devices in different ways. Furthermore, the way data is communicated from one device to another may occur in different ways. In order to illustrate data communication between system devices, let us use the example of a system where the wearable device 449 runs the Protected Qualifying Movement Algorithm 325. In this example configuration, the companion device 401 can send movement data to the wearable device. The nature of the data transmitted by the companion device and the frequency or periodicity of transmission may depend on the application state of the overall system. The companion device 401 may send data to the wearable device 449 in different ways and many approaches for communication between devices are possible.

One way the companion device 401 may transmit data to the wearable device 449 is by streaming data from the sensors. The companion device may systematically and periodically send data taken from the companion device sensors. Many protocol approaches may be used to achieve this data transfer from the companion device 401 to the wearable device 449. For example, the companion device 401 may be queried by the wearable device 449 for data, or the companion device 401 may transmit data based on a predefined schedule. This may require the companion device 401 to spend much of its time transmitting data, and all the calculations identifying pauses, movement, and QMs can then be performed by the microprocessor 321 on the wearable device 449. The companion device 401 may provide pre-processing of the sensor data. Some examples of pre-processing can include: filtering, decimation, interpolation, integration, differentiation, and gain or scaling.

Another way the companion device 401 may transmit data to the wearable device 449 may include differing degrees of processing performed by the processor 321 on the companion device 401. In an example shown in FIGS. 8*a*-8*c* the pauses 269 and user movement 593 from the perspective or sensor output of the companion device can be identified independently by the companion device. With reference to FIG. 8*b*, Evaluation Option 1 shows an evaluation box 593 when the signal processing can be performed to evaluate and identify the user movements. In this example, a first pause 569 may be identified, followed by the user movement 593. Following the user movement 593 the second pause 569 can be detected. The system can then perform a movement evaluation during evaluation box 593. The algorithm may identify the movement duration 592, and compare it against the movement duration limits for a QM 595. If the movement duration 592 is within the preset QM duration 597 limits, the system may calculate movement distance, direction, and orientation from P1 to P2 and report this information to the wearable device 449. The wearable device 449 or other system component may calculate partial data as may be utilized in such QM ID techniques as Position Thresholding and Rotation Thresholding. For example, the wearable device may calculate change in position and orientation moving from P1 to P2 during the movement. This data may then be transmitted to the wearable device to be combined with data from the sensors taken by the wearable device for QM ID as described above with reference to FIGS. 7*a*-7*d*. In an embodiment, time stamps may be used to communicate critical starting and ending instants to the wearable.

With reference to FIGS. 8*a* and 8*c*, Evaluation Option 2 shows an evaluation box 595 starting at or near the identification of the start of a user movement 593 following the first pause 569. The position at the start of the movement is P1. The user movement is evaluated for QM ID for a preset fixed duration 597 as shown in FIG. 8*c*. The end of the preset fixed duration 597 defines the time instant for P2. Changes in position and orientation moving from P1 to P2 may be calculated and QM ID techniques such as Position Thresholding and Rotation Thresholding may be utilized. This user movement data may then be transmitted to the wearable device 449 to be combined with data from the sensors taken by the wearable device 449 for QM ID 599 as described in the example shown in FIG. 7.

In an embodiment, the Protected Qualifying Movement Algorithm 325 is run on the processor 321 in the companion device 401. The wearable 449 may transmit core status data to the companion device 401. In an embodiment, only the core contraction sensor data from the wearable device 449 is utilized by the Protected Qualifying Movement Algorithm 325 and streaming this core contraction sensor data from the wearable 449 to the companion device 401 may be performed.

Another application of the inventive system is shown in FIGS. 9*a* and 9*b* where a user 447 is depicted executing the exercise often referred to as the bench press. The companion device 401 is shown attached to the bar 600. In FIG. 9*a*, the user 447 is in the pre-press position and in FIG. 9*b*, the user 447 is in the fully pressed position. The attachment device 411 may be designed to ensure the companion device 401 substantially holds its orientation throughout the exercise. In other words, the attachment device 411 may be designed so that the companion device 401 does not rotate around the bar 600 during the exercise movements or remains in a vertical orientation relative to the bar 600. For example, the attachment device 411 can include a slotted ring may be made of a flexible material such as rubber to allow the slot to increase in distance to enable the slotted ring to hold onto a bar 600. Furthermore, the inner part of the slotted ring attachment device 411 may have teeth as shown in FIG. 1*g*. These teeth may help the device to minimize rotation around the bar during the exercise to support QM ID using the approach described.

The inventive principles for identifying exercise movements may be extended to applications where the companion device may rotate during movement by extending the movement identification algorithms to three dimensions as one skilled in the art may understand.

In another embodiment, the attachment device for the companion device 401 may be a wrist band 603 as shown in FIG. 1*c* and depicted on the right wrist of a user gripping a bar 553 to perform the lat pull-down exercise as shown in FIG. 10*a*. An embodiment of this user-attached configuration is a smart watch. The perspective of the illustration of FIG. 10*a* is from behind the user 447. P1[$n$] 601 signifies the position and orientation of the companion device 401 at the start of Movement n. A side view of the right hand gripping the bar 553 from the perspective of the user's head is shown in FIG. 10*b*. The xyz-axes with the P1[$n$] 601 at the origin for companion device 401 is shown in FIGS. 10*a*-10*c*. In FIG. 10*c*, P1[$n$] 601 is shown on the xyz-axes in isolation.

The user's hand in the up position during lat pull-downs is shown again in FIG. 11*a* with position-orientation P1[$n$] 601 at the start of the movement. At the end of the pull-down movement, the companion device 401 will be in the position shown as position-orientation P2[n] 602. The Threshold Box 572, 574 is shown in FIG. 11b comprised of cylindrical volumes above and below the origin and starting position P1[n] 601. If P2 [n] 602 is enclosed by Threshold Box cylindrical volume 574, the movement will be identified as a QM. In order to complete the repetition, the user 447 will perform the release-up movement which is Movement n+1. The next repetition will be Movement n+2 with starting position-orientation P1[n+2]. The Threshold Box cylindrical volumes 572, 574 will be positioned relative to P1[k] for Movement k.

With most exercises, there is a movement in one direction followed by a movement in the opposite direction of similar distance. And in general, when the exercises are done properly, there is a pause in between the movements. These are examples of observations that may be implemented into the algorithms and algorithm controllers to infer exercise movements and accordingly encourage a user to utilize their core during such exercise movements.

In FIGS. 12b-12c, diagrams of the user's hands moving down and up during repetitions of the pull-down and release-up movements of the lat pull-down exercise are shown. The xyz-axes of FIGS. 10 and 11 are shown referenced to the wearable device 449 at P1[n]. In FIG. 12a, a new coordinate system X'Y'Z' is shown where Z' is perpendicular to the earth and the X'Y'-plane is parallel to the earth. Using trigonometry, movements in one coordinate system may be translated into movements in the other coordinate system. This may allow movements up and down in the Z'-dimension to be tracked in isolation and plotted in FIGS. 12b and 12c. Movements 607, 609 are identified between pauses 569 as shown in FIG. 12b. Movement n 607 results from a pull-down movement and Movement n+1 609 results from a release-up movement. Let us consider the Z'-dimension position 610 shown as a function of time, moving downwards during the pull-down movement and upwards during the release-up movement. Movements will generally be in three dimensions. Let us use this Z'-dimension description to illustrate the key principles which can be applied to the general three dimensional case as one skilled in the art would understand. Suppose the Z'-dimension position 610 change in the first pull-down movement is minus 12 inches. In the illustrated example, the Z'-dimension position 610 change in the first release-up movement is plus 12 inches. In practical implementations, due to finite accuracy in the movement detection algorithms and any irregularity in the actual hand movements, the Z'-dimension position 610 changes may not be exact; instead they may be similar or substantially similar. This makes defining the Threshold Box in the shape of a cylinder attractive as used in examples referring to FIGS. 6 and 11 to accommodate X' and Y'-axis movements along with the Z'-axis movements. Appropriate thresholds defining the Threshold Box may be relative to the movement magnitude, fixed, or adaptive. When a movement is followed by a movement of similar magnitude but in the opposite direction, it is possible that the user is performing one repetition of an exercise. The Z'-dimension position 610 of the companion device during three repetitions of the lat pull-down exercise are shown in FIG. 12c. After the first pull-down movement, since the following release-up movement is similar in distance and opposite in direction, a repetition of an exercise movement is likely. Since the detected second pull-down movement is similar in direction and distance to the first detected second pull-down movement, this may further increase the likelihood that the user is performing repetitions of an exercise.

Algorithms may be designed to utilize movement direction or orientation to identify patterns of movement that typically exist in gym exercises performed on exercise machines. Alternatively, algorithms may be designed to utilize available data including orientation, movement, user state, patterns of movement, changes in orientation, and changes in movement to further increase the quality of movement identification algorithms.

This description includes examples of the broad range of available sensor data and examples of how the identification of repetitive patterns and movements in one trajectory followed by movements in substantially the opposite trajectory may be utilized to improve the quality of QM ID and more specifically, exercise movement identification. This description is not meant to be a complete description of how data from the sensors on the wearable device and companion device may be used, but through illustrative examples, the description demonstrates how movements and orientations can be combined over time to improve the quality of the algorithms to achieve their intended objectives.

Figure 13B:
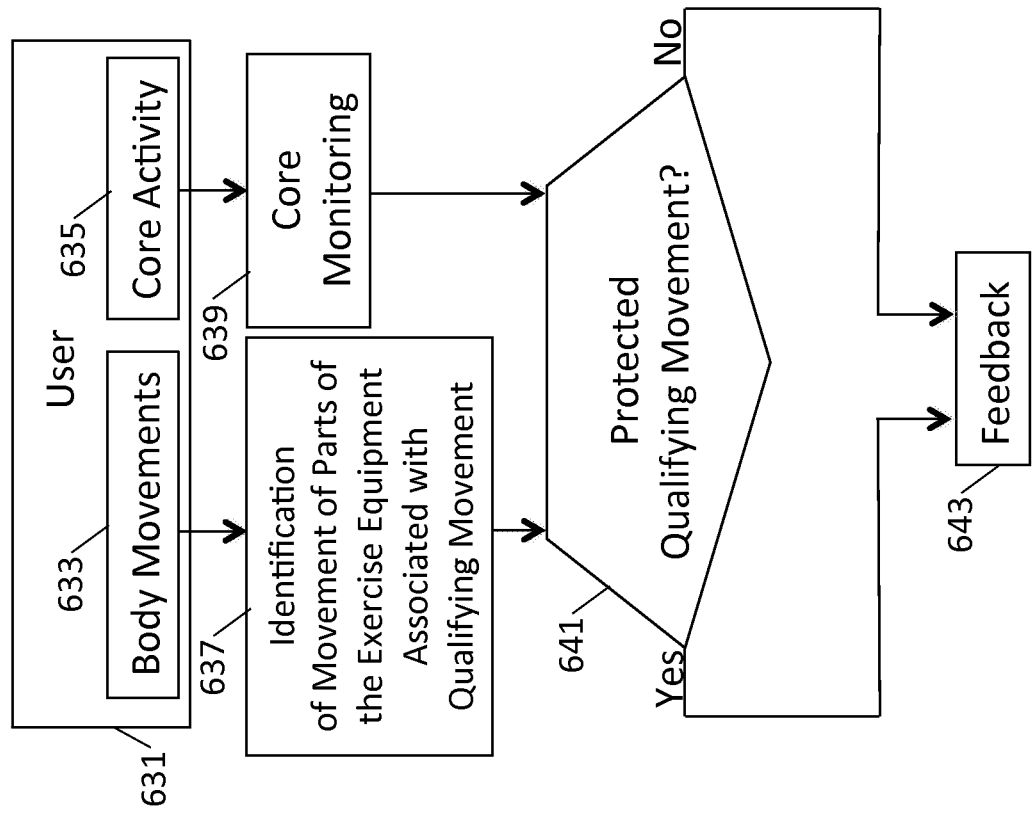
Figure 13A:
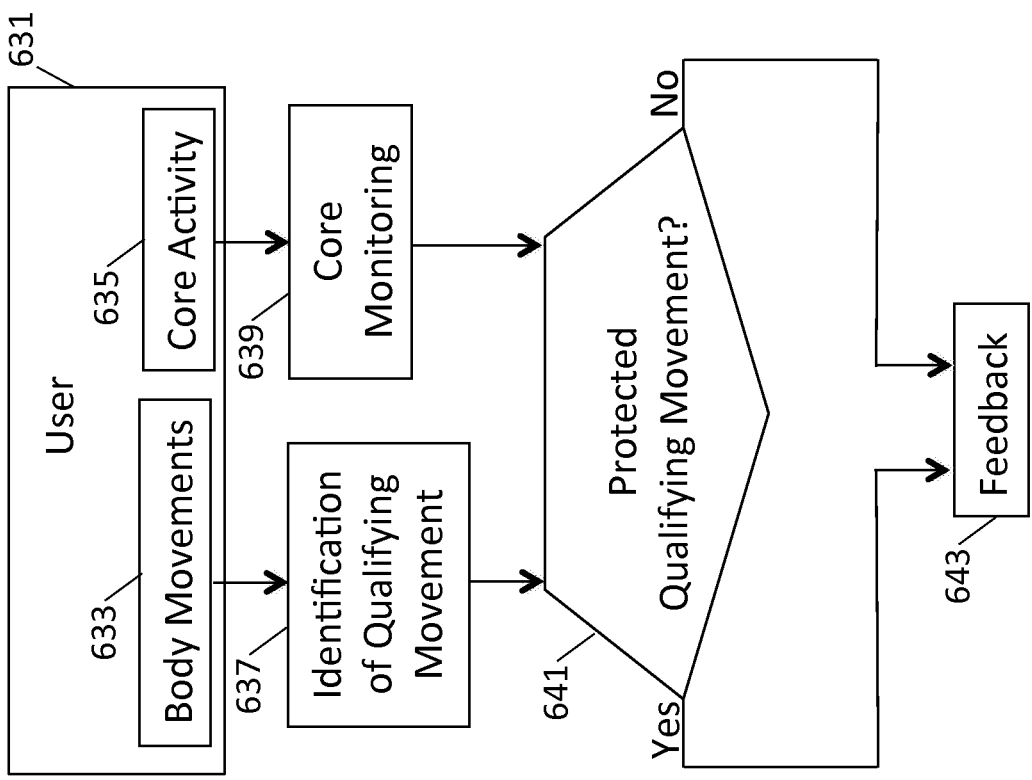
Figure 13C:
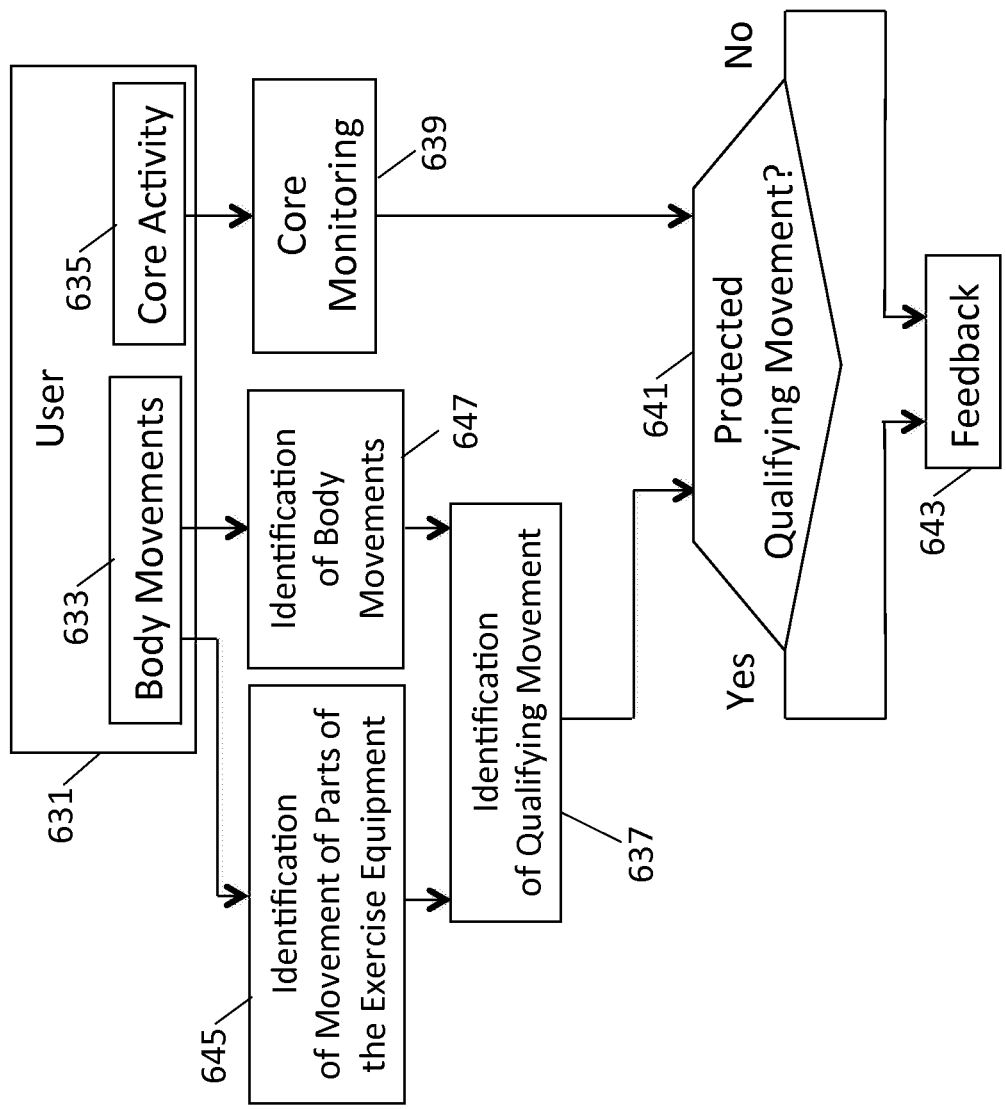
Figure 13D:
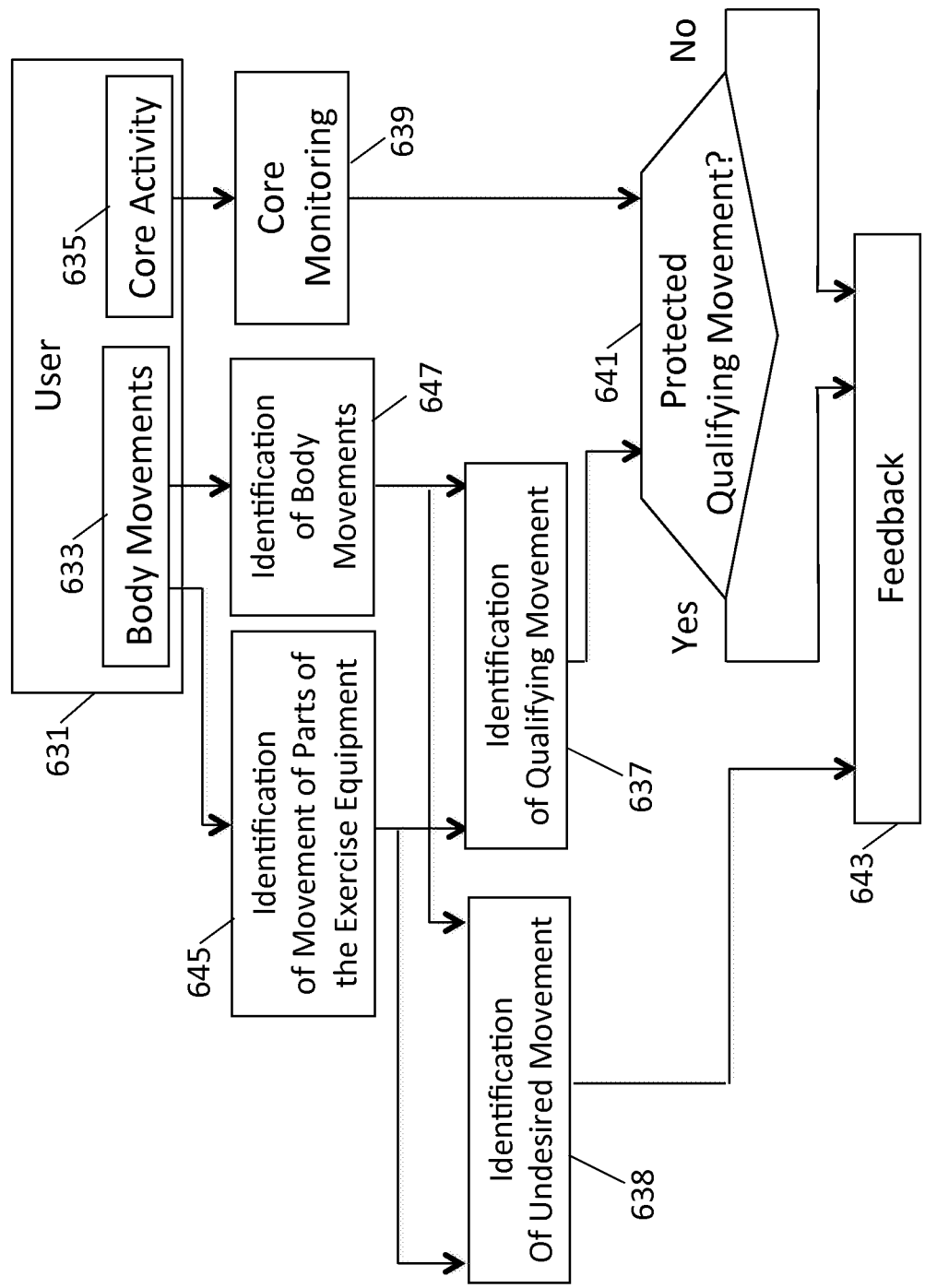

A high level functional block diagram is shown in FIG. 13a where a user's 631 body movements 633 and core activity 635 are input to two blocks, a first block identifies Qualifying Movements 637 based on the body movements of the user and a second block identifies and monitors core activity 635 for core contraction. When a Qualifying Movement is detected, the QM is compared with the output of the core monitoring function to determine whether or not the QM was protected or unprotected 641. Based on the result, feedback 643 may be provided to the user. In FIG. 13b, a similar functional diagram is presented with the difference that the identification of Qualifying Movements is replaced by a functional block that identifies movements of parts of exercise equipment and associates these movements with Qualifying Movements 645. In FIG. 13c, both a user's body movements 647 and the identification of movements of parts of exercise equipment 645 are combined to identify a Qualifying Movement 637. In FIG. 13d, the diagram of FIG. 13c is shown with the addition that undesired body movements may be identified 638 during an exercise movement and feedback 543 may be provided. An example of undesired movements during an exercise may be rocking the torso during lat pull-downs.

In FIG. 14, a high level signal processing block diagram is shown for the system with a wearable device and a companion device. Body movements and core activity 651 for a user are input to two paths. One path goes to a first sensor group 655 which may have multiple sensors. The outputs of this group of sensors may be transmitted to a core contraction identifier 663 to identify core contractions and a body position, orientation, and movement identifier to identify 661 to identify a user's body position, orientation, and movement. In the second path, the user's body movements while performing an exercise may cause the movement of parts or components of the exercise equipment 653. This exercise equipment movement may be detected by a second group of sensors 657 that may also be comprised of multiple sensors that may be used to identify position, orientation, and movement of the companion device. The body movement data from the wearable device and the companion device movement data may be combined to identify a Qualifying Movement 665. When a Qualifying Movement is detected, the Movement Discriminator 631 may compare the timing of the Qualifying Movement with timing of the contraction of the user's core and determine whether or not the movement is protected or unprotected. A feedback controller 669 may then generate the appropriate feedback signal 671. The system can use the feedback signal 671 to notify the user if the Qualifying Movement has been performed with or without the core so that the user knows if the Qualifying Movement was protected or unprotected.

In FIG. 15*a*, an embodiment of a signal flowchart is shown. Body movements translated into exercise machine or equipment movements are monitored with sensors in a companion device and core activity is monitored with sensors in a wearable device 681. Using communication devices, the movement and core contraction data is combined onto one device 683. If a movement is identified as a Qualifying Movement, the system can then perform discriminating or comparing the timing relationship between the Qualifying Movement and the core contraction. The system may determine whether or not the Qualifying Movement was protected or unprotected 685. Based on this signal processing, the system may provide feedback to the user 689 to notify the user if the Qualifying Movement has been performed with or without the core so that the user knows if the Qualifying Movement was protected or unprotected.

In FIG. 15*b*, another embodiment of a signal flowchart with the difference that body movement data from the wearable device is used 691. This data may be combined with the movement data from the companion device to improve the quality and reliability of the exercise movement identification. In many applications, when a movement is performed on exercise equipment, the torso should have little movement. If significant movement is detected during an exercise movement, the user may not be performing an exercise movement on exercise equipment.

FIG. 15*c* illustrates another embodiment of a signal flowchart. As a user is carrying the companion device and wearing the wearable in the gym, they will make many arbitrary movements. Random movements may trigger false QM IDs. Once a user is performing an exercise, the movements on the exercise machine or equipment will be quite regular with the companion device moving in one direction during the first movement of the exercise and then in the opposite direction during the second movement of the exercise. The described approach may improve identifying when the user begins performing exercise movements. The first repetition may not have an immediate feedback, but subsequent repetitions in a set may have immediate feedback. Since data associated with the first repetition may be stored in memory, the data may be retrieved to identify protected and unprotected movements during the first repetition.

Referring to FIG. 15*c*, exercise machine or equipment movements are monitored with sensors in a companion device and core contraction activity is monitored with sensors in a wearable device 681. Using movement sensors in the companion device, identify a first Qualifying Movement, a Pause, then a Second Qualifying Movement. Store the movement data and core contraction data in memory. Then, check if the second movement is substantially opposite in direction or trajectory and similar in distance to the first movement 684. If the second movement is substantially opposite in direction and similar in distance to that of the first movement 692, continue evaluating subsequent movements 686. If the direction of the second movement is not substantially opposite in direction and similar in distance to the first movement 692, we may assume the first movement was not an exercise movement and return to the beginning. In some embodiments, before evaluating subsequent movements, the processor running the Protected Qualifying Movement Algorithm 325 may retrieve the relevant data to evaluate the first two movements to determine if they were protected movements or unprotected movements and report this to the user 447.

Core contraction activity and exercise machine or equipment movements are monitored 681 and when a Qualifying Movement is identified, a check is made to see if it is in a substantially opposite in direction or trajectory and similar in distance to the previous movement 688. If the movement is substantially opposite in direction and similar in distance to the previous movement, prepare to discriminate the movement 683. If the movement does not meet the test of being substantially opposite in direction and similar in distance to the previous movement, the signal flow may stop and return to the beginning. If the movement meets the test, then discriminate the movement to determine if the movement is protected or unprotected 685 and provide feedback to the user 689.

In an embodiment, a movement that does not meet the test of being substantially opposite in direction and similar in distance to the previous movement may be tested to be greater than a minimum threshold. And only if the magnitude is larger than this threshold and it fails the direction and distance test will the signal flow return to the start. If the magnitude is not larger than the threshold, the system will continue and evaluate the next identified qualifying movement to check if it is substantially opposite in direction and similar in distance to the previous validated movement. This example is one of many modifications that may be implemented to identify a false failure of the direction and magnitude test where a false failure is an incorrect determination that an exercise set has been completed.

The figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical functions. It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems which perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or" comprising," when used in this specification, specify the presence of stated features, integers, steps, operations, elements, and/or components, but do not preclude the presence or addition of one or more other features, integers, steps, operations, elements, components, and/or groups thereof.

Some embodiments of the invention are implemented as a program product for use with an embedded processor. The program(s) of the program product defines functions of the embodiments (including the methods described herein) and can be contained on a variety of signal-bearing media.

Illustrative signal-bearing media include, but are not limited to: (i) information permanently stored on non-writable storage media; (ii) alterable information stored on writable storage media; and (iii) information conveyed to a computer by a communications medium, such as through a computer or telephone network, including wireless communications. The latter embodiment specifically includes information downloaded from the Internet and other networks. Such signal-bearing media, when carrying computer-readable instructions that direct the functions of the present invention, represent embodiments of the present invention.

In general, the routines executed to implement the embodiments of the invention, may be part of an operating system or a specific application, component, program, module, object, or sequence of instructions. The computer program of the present invention typically is comprised of a multitude of instructions that will be translated by the native computer into a machine-accessible format and hence executable instructions. Also, programs are comprised of variables and data structures that either reside locally to the program or are found in memory or on storage devices. In addition, various programs described hereinafter may be identified based upon the application for which they are implemented in a specific embodiment of the invention. However, it should be appreciated that any particular program nomenclature that follows is used merely for convenience, and thus the invention should not be limited to use solely in any specific application identified and/or implied by such nomenclature.

The present invention and some of its advantages have been described in detail for some embodiments. It should be understood that although the process is described with reference to a device, system, and method for developing core contraction procedural memory, the process may be used in other contexts as well. It should also be understood that various changes, substitutions and alterations can be made herein without departing from the spirit and scope of the invention as defined by the appended claims. An embodiment of the invention may achieve multiple objectives, but not every embodiment falling within the scope of the attached claims will achieve every objective. Moreover, the scope of the present application is not intended to be limited to the particular embodiments of the process, machine, manufacture, composition of matter, means, methods and steps described in the specification. A person having ordinary skill in the art will readily appreciate from the disclosure of the present invention that processes, machines, manufacture, compositions of matter, means, methods, or steps, presently existing or later to be developed are equivalent to, and fall within the scope of, what is claimed. Accordingly, the appended claims are intended to include within their scope such processes, machines, manufacture, compositions of matter, means, methods, or steps.

What is claimed is:

1. A system for development of core muscle support, comprising:
    a companion device adapted to be worn on a wrist of a user having a first sensor in communication with a processor for identifying an arm movement of the user;
    a wearable device having a core muscle sensor in communication with the processor for detecting a core muscle contraction of the user, wherein the wearable device is not in direct physical contact with the companion device;
    a qualifying movement algorithm running on the processor for discriminating between a qualifying arm movement that benefits from the core muscle contraction and a non-qualifying arm movement that does not benefit from the core muscle contraction based upon arm movement signals from the first sensor;
    a movement discriminator running on the processor for identifying protected qualifying arm movements where the core muscle contraction is detected by the core muscle sensor during the qualifying arm movement and an unprotected qualifying arm movement where the core muscle contraction is not detected by the core muscle sensor during the qualifying arm movement; and
    a feedback device in communication with the processor that provides feedback to the user when the unprotected qualifying arm movement is detected by the movement discriminator.

2. The system of claim 1 wherein the companion device further comprises an attachment device for securing the companion device to the user.

3. The system of claim 2 wherein attachment device includes: a band, a hook, a loop or a ring.

4. The system of claim 1 wherein the companion device includes a wireless transmitter for transmitting the arm movement signals to the processor.

5. A system for development of core muscle support, comprising:
    a companion device adapted to be worn on a wrist of a user having a first sensor in communication with a processor, the first sensor providing arm movement signals for identifying arm movements of the user;
    a wearable device having a core muscle sensor in communication with the processor for detecting core muscle contractions of the user, wherein the wearable device is not in direct physical contact with the companion device;
    a qualifying movement algorithm running on the processor that receives the arm movement signals from the first sensor, wherein the qualifying movement algorithm identifies the arm movements of the user that are qualifying movements that benefit from the core muscle contractions and the arm movements of the user that are non-qualifying movements that do not benefit from the core muscle contractions;
    a movement discriminator running on the processor for identifying protected qualifying movements where the core muscle contractions are detected by the core muscle sensor during the qualifying movements and unprotected qualifying movements where the core muscle contractions are not detected by the core muscle sensor during the qualifying movements based upon the movement signals from the first sensor; and
    a feedback device in communication with the processor that provides feedback to the user for each of the protected qualifying movements or each of the unprotected qualifying movements.

6. The system of claim 5 wherein the companion device comprises an attachment device adapted for attaching the companion device to the user.

7. The system of claim 6 wherein the attachment device includes: a strap, a band, a hook, a loop or a ring.

8. The system of claim 5 wherein the companion device includes a wireless transmitter for transmitting the movement signals to the processor.

9. The system of claim 5 wherein the companion device includes a housing, a printed circuit board and a rechargeable battery.

10. The system of claim 5 wherein the first sensor is a gyro.

11. The system of claim 5 wherein the first sensor is a 3-axis accelerometer.

12. The system of claim 5 wherein the first sensor is a gyro and the companion device includes a second sensor which is a 3-axis accelerometer in communication with the processor.

\* \* \* \* \*